United States Patent
Broquaire et al.

(10) Patent No.: US 7,405,323 B2
(45) Date of Patent: Jul. 29, 2008

(54) MODAFINIL POLYMORPHIC FORMS

(75) Inventors: Michel Broquaire, deceased, late of Le Perreux (FR); by Véronique Broquaire, legal representative, Noisy-le-Grand (FR); by Ludovic Broquaire, legal representative, Frejus (FR); Laurent Courvoisier, Laigneville (FR); Gerard Coquerel, Boos (FR); Franck Mallet, Blangy sur Bresle (FR)

(73) Assignee: Cephalon France, Maisons Alfort (FR)

( * ) Notice: Subject to any disclaimer, the term of this patent is extended or adjusted under 35 U.S.C. 154(b) by 0 days.

(21) Appl. No.: 11/248,442

(22) Filed: Oct. 12, 2005

(65) Prior Publication Data

US 2006/0252835 A1    Nov. 9, 2006

Related U.S. Application Data

(63) Continuation of application No. 10/635,445, filed on Aug. 7, 2003, now Pat. No. 6,992,219.

(60) Provisional application No. 60/402,064, filed on Aug. 9, 2002.

(51) Int. Cl.
C07C 233/05   (2006.01)
A61K 31/165   (2006.01)

(52) U.S. Cl. ...................... 564/162; 514/618

(58) Field of Classification Search .......... 564/162; 514/618
See application file for complete search history.

(56) References Cited

U.S. PATENT DOCUMENTS

| | | | |
|---|---|---|---|
| 4,177,290 A | 12/1979 | Lafon | 424/324 |
| 4,927,855 A | 5/1990 | Lafon | 514/618 |
| 5,180,745 A | 1/1993 | Lafon | 514/618 |
| 5,391,576 A | 2/1995 | Lafon | 514/618 |
| 5,401,776 A | 3/1995 | Laurent | 514/618 |
| 5,612,379 A | 3/1997 | Laurent | 514/618 |
| 5,719,168 A | 2/1998 | Laurent | 514/357 |
| RE37,516 E | 1/2002 | Grebow et al. | 514/618 |
| 6,875,893 B2 * | 4/2005 | Largeau et al. | 564/162 |
| 2003/0077297 A1 | 4/2003 | Chen et al. | 424/400 |
| 2003/0114470 A1 | 6/2003 | Wizel et al. | 514/263.38 |
| 2003/0180352 A1 | 9/2003 | Patel et al. | 424/465 |
| 2004/0102523 A1 | 5/2004 | Broquaire et al. | 514/618 |
| 2004/0229940 A1 | 11/2004 | Hassman et al. | 514/469 |
| 2004/0229941 A1 | 11/2004 | Hassman et al. | 514/469 |
| 2004/0229942 A1 | 11/2004 | Hassman et al. | 514/469 |
| 2004/0229943 A1 | 11/2004 | Hughes et al. | 514/469 |
| 2004/0242698 A1 | 12/2004 | Hughes | 514/618 |

FOREIGN PATENT DOCUMENTS

| | | |
|---|---|---|
| EP | 1477476 A8 | 11/2004 |
| WO | WO 99/25329 A1 | 5/1999 |
| WO | WO 00/54648 A3 | 9/2000 |
| WO | WO 01/12170 A3 | 2/2001 |
| WO | WO 01/13906 A3 | 3/2001 |
| WO | WO 02/10125 A1 | 2/2002 |
| WO | WO 2004/101503 A1 | 11/2004 |

OTHER PUBLICATIONS

Bastuji, H., et al., "Successful treatment of idiopathic hypersomnia and nacrolepsy with modafinil," *Prog. Neuropsych. Biol. Psych.*, 1988, 12, 695-700.
Drabowics, J., et al., "A convenient procedure for the oxidation of sterically hindered sulfides to sulfoxides," *Synthesis*, 1990, 937-938.
Duteil, J., et al., "Central $\alpha_1$-adrenergic stimulation in relation to the behaviour stimulating effect of modafinil; studies with experimental animals," *Eur. J. Pharmacol.*, 1990, 180, 49-58.
Examiner's Search for U.S. Appl. No. 10/635,445.
Haleblian, J.K., "Characterization of Habits and crystalline modification of solids and their pharmaceutical applications," *J. of Pharm. Sciences*, 1975, 64(8), 1269-1288.

* cited by examiner

*Primary Examiner*—Shailendra Kumar
(74) *Attorney, Agent, or Firm*—Woodcock Washburn LLP

(57) ABSTRACT

Modafinil polymorphic forms of modafinil racemate, methods of preparation thereof, pharmaceutical compositions and methods of therapeutic treatment involving modafinil polymorphic forms.

19 Claims, 13 Drawing Sheets

MODAFINIL POLYMORPHIC FORMS

The present invention relates to modafinil polymorphic forms, methods of preparation thereof, pharmaceutical compositions and methods of therapeutic treatment involving modafinil polymorphic forms.

BACKGROUND OF THE INVENTION

Modafinil ($C_{15}H_{15}NO_2S$) of formula I, 2-(benzhydrylsulfinyl) acetamide, or 2-[(diphenylmethyl)sulfinyl]acetamide, is a synthetic acetamide derivative with wake-promoting activity, the structure of which has been described in U.S. Pat. No. 4,177,290 ("the '290 patent"), and whose racemate has been approved by the United States Food and Drug Administration for use in the treatment of narcolepsy.

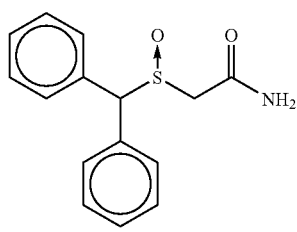

Formula (I)

A method of preparation of a racemic mixture is described in the '290 patent. A method of preparation of a levorotary isomer is further described in the U.S. Pat. No. 4,927,855 (both incorporated herein by reference).

Modafinil has been described as a compound having an interesting neuropsychopharmacological potential in mouse (U.S. Pat. No. 4,177,290). Modafinil also induces an important increase in night activity of monkey (Y. Duteil et al., Eur. J. Pharmacol., 1990; 180:49). Modafinil has been successfully tested in humans for treatment of idiopathic hypersomnia and narcolepsy (Bastuji et al., Prog. Neuropsych. Biol. Psych., 1988; 12:695).

Modafinil has also been described as an agent with activity on the central nervous system, and as a useful agent in the treatment of Parkinson's disease (U.S. Pat. No. 5,180,745), in the protection of cerebral tissue from ischemia (U.S. Pat. No. 5,391,576), in the treatment of urinary and fecal incontinence (U.S. Pat. No. 5,401,776), and in the treatment of sleep apneas and disorders of central origin (U.S. Pat. No. 5,612,379).

U.S. Pat. No. Re. 37,516 describes modafinil preparations of a defined particle size of less than about 200 microns that are more effective and safer than preparations containing a substantial proportion of larger particles.

Beside, these patents that relate to modafinil as racemate, U.S. Pat. No. 4,927,855 discloses the use of the levorotary isomer to treat depression, and disorders present in patients suffering from Alzheimer's disease.

Other therapeutic indications that relate to modafinil racemate are disclosed in more recent patent applications. For instance, international patent application. WO 00/54648 relates to the treatment of vigilance disorders of Steinert's disease, and international patent application WO 99/25329 relates to the treatment of hypersomnia in cancer patients that are administered with morphinic antalgics. Other known therapeutic indications include the treatment of attention deficit hyperactivity disorders (ADHD) linked to hyperactivity and treatment of tiredness and/or fatigue, particularly tiredness and/or fatigue associated to multiple sclerosis (international patent application WO 01/12170), as well as treatment of food behaviour disorders, wherein modafinil is active as an appetite stimulant (international patent application WO 01/13906). International patent application WO 01/13906 also suggests using low doses of modafinil (1 to 75 mg/day) to stimulate cognitive functions, without observing any improvement at higher doses.

The international patent application WO 02/10125 discloses polymorphs of modafinil and processes for preparing them.

SUMMARY OF THE INVENTION

The present invention provides five novel polymorphic forms of modafinil racemate called CRL 40476 form III (CRL 40476-[f III]), CRL 40476 form IV (CRL 40476-[f IV]), CRL 40476 form V (CRL 40476-[f V]) and CRL 40476 form VI (CRL 40476-[f VI]), CRL 40476 form VII (CRL 40476-[f VII]) (also abbreviated as forms III, IV, V, VI and VII) and modafinil solvates. Significant physical, pharmaceutical, physiological or biological differences with form I (CRL 40476-[f I]) have been shown.

Accordingly, the invention also provides methods for preparing these forms and a new solvate of modafinil, i.e acetonitrile. Moreover, this invention also describes other new modafinil species of a modafinil solvate solid solution.

The invention also provides pharmaceutical compositions containing these forms. In particular a composition containing form IV and a composition containing form V are provided.

The invention also provides methods of treatment of diseases or symptoms wherein modafinil is useful. In particular, these new methods are for similar therapeutic indications to those described in the above identified patents and applications and are incorporated herein by reference.

The invention also provides methods for preparing novel forms and compositions.

DETAILED DESCRIPTION

Pursuing experimental work for improving the manufacturing and treating the starting drug substance by crystallization in varying physico-chemical conditions (such as crystallization solvent, temperature, concentration, filtration methods . . . ), the Inventors have now identified five novel polymorphic forms of modafinil racemate, they called CRL 40476 form III (CRL 40476-[f III]), CRL 40476 form IV (CRL 40476-[f IV]), CRL 40476 form V (CRL 40476-[f V]), CRL 40476 form VI (CRL 40476-[f VI]) (CRL 40476 form VII (CRL 40476-[f VII]) (also abbreviated as forms III, IV, V, VI and VII).

Figure 1:
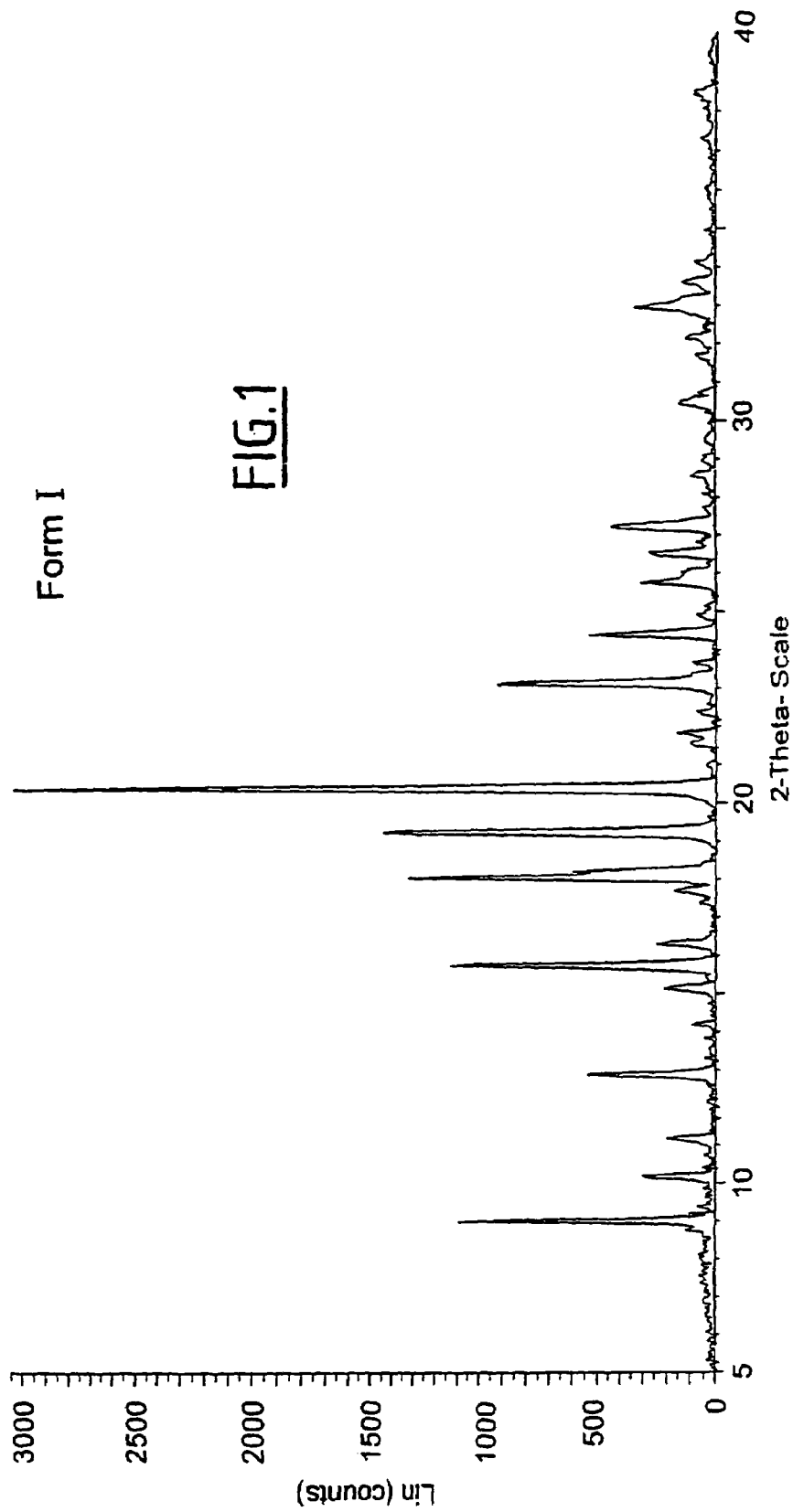
FIG. 1 represents a powder X-ray diffraction pattern of CRL 40476 form I.

The Inventors have further discovered that modafinil prepared by the method described in '290 patent' is produced in the form of a polymorph which is hereinafter referred to as 'CRL 40476 form I' (or CRL 40476-[f I]). CRL 40476 form I has the following powder X-ray diffraction pattern (FIG. 1), wherein d represents the interplanar spacing and I/I$_0$ the relative intensity:

| 2 Theta (degrees) | d (Å) | I/I$_0$ (%) |
| --- | --- | --- |
| 8.99 | 9.83 | 42 |
| 10.16 | 8.70 | 18 |
| 11.12 | 7.95 | 14 |
| 12.85 | 6.88 | 24 |
| 15.14 | 5.85 | 13 |
| 15.73 | 5.63 | 41 |
| 16.32 | 5.43 | 13 |
| 17.71 | 5.00 | 11 |
| 18.06 | 4.91 | 47 |
| 19.23 | 4.61 | 50 |
| 20.38 | 4.35 | 100 |
| 21.58 | 4.12 | 8 |
| 21.84 | 4.07 | 10 |
| 22.39 | 3.97 | 7 |
| 23.12 | 3.84 | 33 |
| 23.63 | 3.76 | 7 |
| 24.44 | 3.64 | 20 |
| 25.80 | 3.450 | 13 |
| 26.04 | 3.419 | 8 |
| 26.55 | 3.354 | 12 |
| 27.26 | 3.268 | 17 |
| 27.69 | 3.219 | 5 |
| 28.59 | 3.119 | 6 |

An unstable polymorph, called modafinil form II, was also identified.

The inventors have further unexpectedly shown that these polymorphs exhibited physical, pharmaceutical, physiological or biological characteristics that were significantly different from form I.

The new crystalline forms of modafinil have been characterized respectively by powder X-ray diffraction spectroscopy which produces a fingerprint that is unique to the crystalline form and is able to distinguish it from the amorphous modafinil and all other crystalline forms of modafinil.

X-ray diffraction data were measured using a D5005 system as a powder X-ray diffractometer (Siemens, AG, Karlsruhe, Germany, data method Eva 5.0), with Ni filtered copper radiation of $\lambda$=1.540 Å (at an accelerator rate of 40 KV, tube current of 40 mA) with spinning rotation of sample during the measurement (angle: 3 to 40 degrees [2 theta]; at a rate of 0.04 degrees [2 theta].s$^{-1}$, the step size being 0.04 degrees; sample preparation with preferential orientation). It will be understood that the intensity values may vary depending upon the sample preparation, the mounting procedure and the instrument variations. The 2 theta measurement may also be affected by instrument variations, consequently the peak assignments may vary by plus or minus 0.04 degrees. Therefore, those skilled in the art will appreciate that the d-spacing constitutes the essence of the diffraction pattern. The d-spacing is calculated using the Bragg relation [(2 d sin theta=n$\lambda$, where d=d-spacing (Å), $\lambda$=wavelength of copper radiation, theta=rotation angle of the crystal (degree)] when satisfied.

Specific surface areas of different polymorphic forms of modafinil were also measured by recording N$_2$ adsorption isotherms and using Brunauer, Emett and Teller (B.E.T) method for calculation (Coulter TM SA 3100 TM Analyser).

Novel Polymorphic Forms of Modafinil

Modafinil Form III (CRL 40476-[f III])

Figure 2:
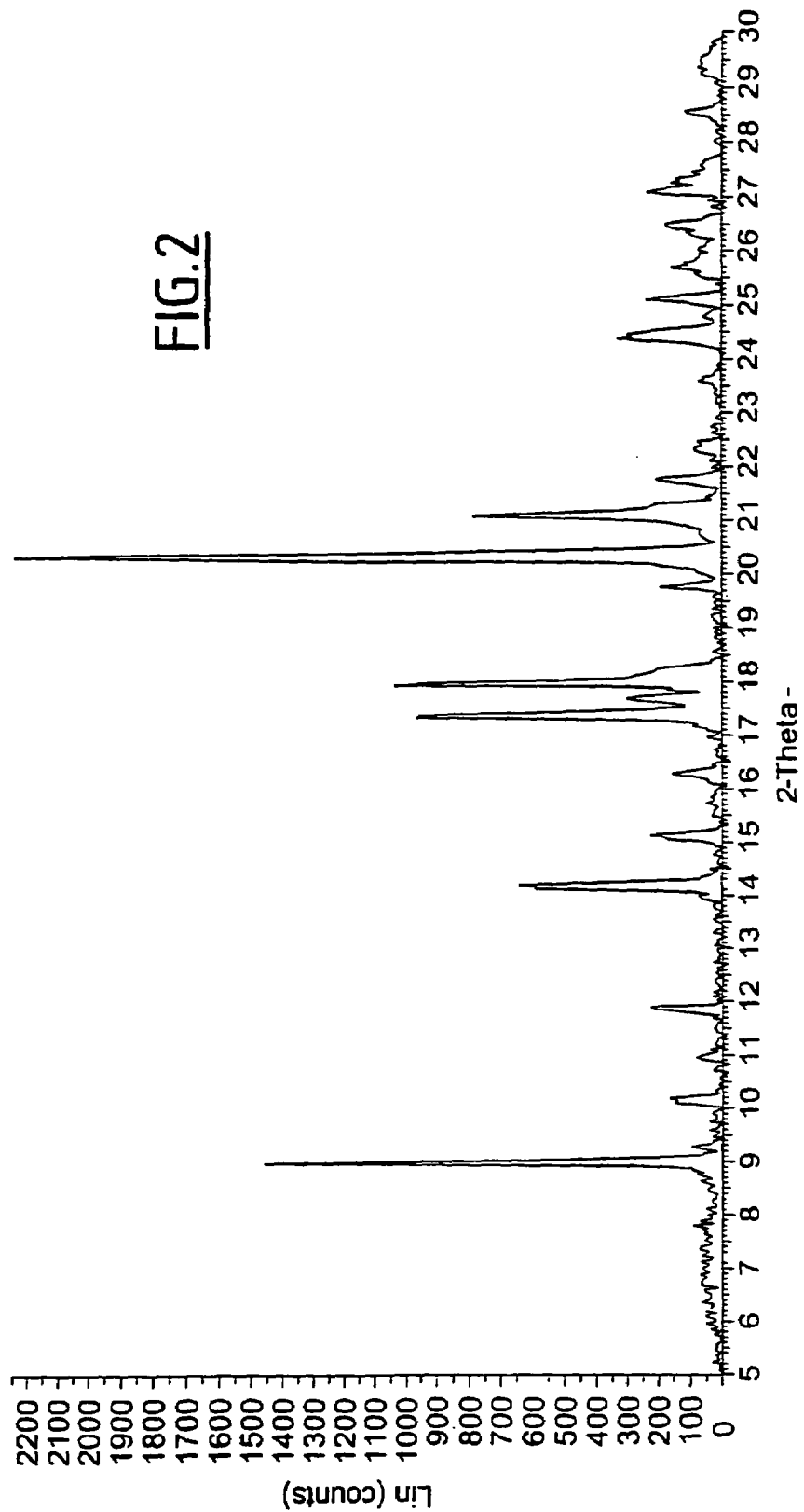
FIG. 2 represents a powder X-ray diffraction pattern of CRL 40476 form III.

The present invention also provides CRL 40476 form III (FIG. 2).

CRL 40476 form III produces a powder X-ray diffraction pattern, wherein d represents interplanar spacing and I/I$_0$ the relative intensity:

| 2 Theta (degrees) | d (Å) | I/I$_0$ (%) |
| --- | --- | --- |
| 8.95 | 9.87 | 72 |
| 10.11 | 8.74 | 19 |
| 10.92 | 8.09 | 15 |
| 11.84 | 7.47 | 20 |
| 14.16 | 6.25 | 37 |
| 15.08 | 5.87 | 19 |
| 16.25 | 5.45 | 15 |
| 17.40 | 5.09 | 48 |
| 17.66 | 5.02 | 21 |
| 17.97 | 4.93 | 51 |
| 19.76 | 4.49 | 16 |
| 20.35 | 4.36 | 100 |
| 21.10 | 4.21 | 40 |
| 21.76 | 4.08 | 16 |
| 22.36 | 3.97 | 10 |
| 23.61 | 3.76 | 9 |
| 24.44 | 3.64 | 19 |
| 25.14 | 3.54 | 15 |
| 25.74 | 3.458 | 12 |
| 26.52 | 3.358 | 13 |
| 27.12 | 3.285 | 15 |
| 28.59 | 3.119 | 9 |
| 29.6 | 3.039 | 8 |

The interplanar d-spacings of 9.87, 6.25, 5.09, 4.93, 4.36, 4.21 (Å) are particularly characteristic.

Of these, the interplanar d-spacings of 9.87, 6.25, 5.09, 4.93, 4.36 (Å) are the most characteristic.

Modafinil form III has a melting decomposition temperature of 159° C.

Modafinil Form IV (CRL 40476-[f IV])

Figure 3:
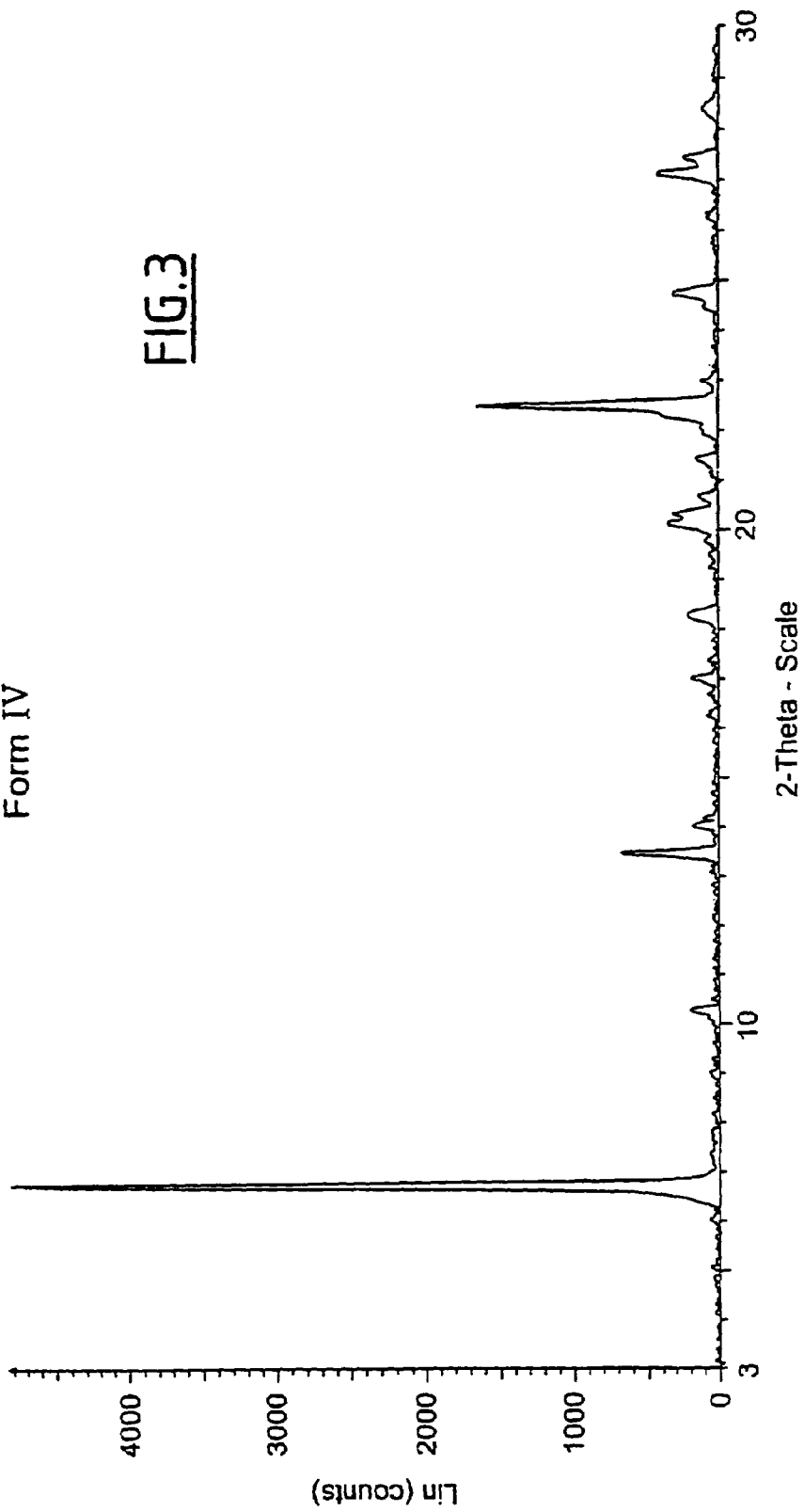
FIG. 3 represents a powder X-ray diffraction pattern of CRL 40476 form IV.

The present invention also provides CRL 40476 form IV (FIG. 3).

CRL 40476 form IV produces the following powder X-ray diffraction pattern, wherein d represents interplanar spacing and I/I$_0$ the relative intensity:

| 2 Theta (degrees) | d (Å) | I/I₀ (%) |
|---|---|---|
| 6.04 | 14.6 | 5 |
| 6.72 | 13.1 | 100 |
| 10.27 | 8.60 | 9 |
| 13.48 | 6.57 | 18 |
| 14.04 | 6.30 | 8 |
| 16.28 | 5.44 | 5 |
| 16.99 | 5.21 | 7 |
| 18.27 | 4.85 | 7 |
| 20.14 | 4.41 | 10 |
| 20.68 | 4.29 | 5 |
| 21.43 | 4.14 | 6 |
| 22.04 | 4.03 | 5 |
| 22.51 | 3.95 | 35 |
| 22.98 | 3.87 | 5 |
| 24.76 | 3.59 | 9 |
| 26.30 | 3.386 | 4 |
| 27.13 | 3.284 | 11 |
| 27.47 | 3.245 | 7 |
| 28.42 | 3.138 | 4 |

The interplanar d-spacings of 13.1, 6.57, 3.95 (Å) are particularly characteristic.

Of these, the interplanar d-spacings of 13.1, 3.95 (Å) are most characteristic.

Modafinil form IV has a melting decomposition temperature of 161° C., which is a characteristic of this polymorph.

Modafinil Form V (CRL 40476-[f V])

Figure 4:
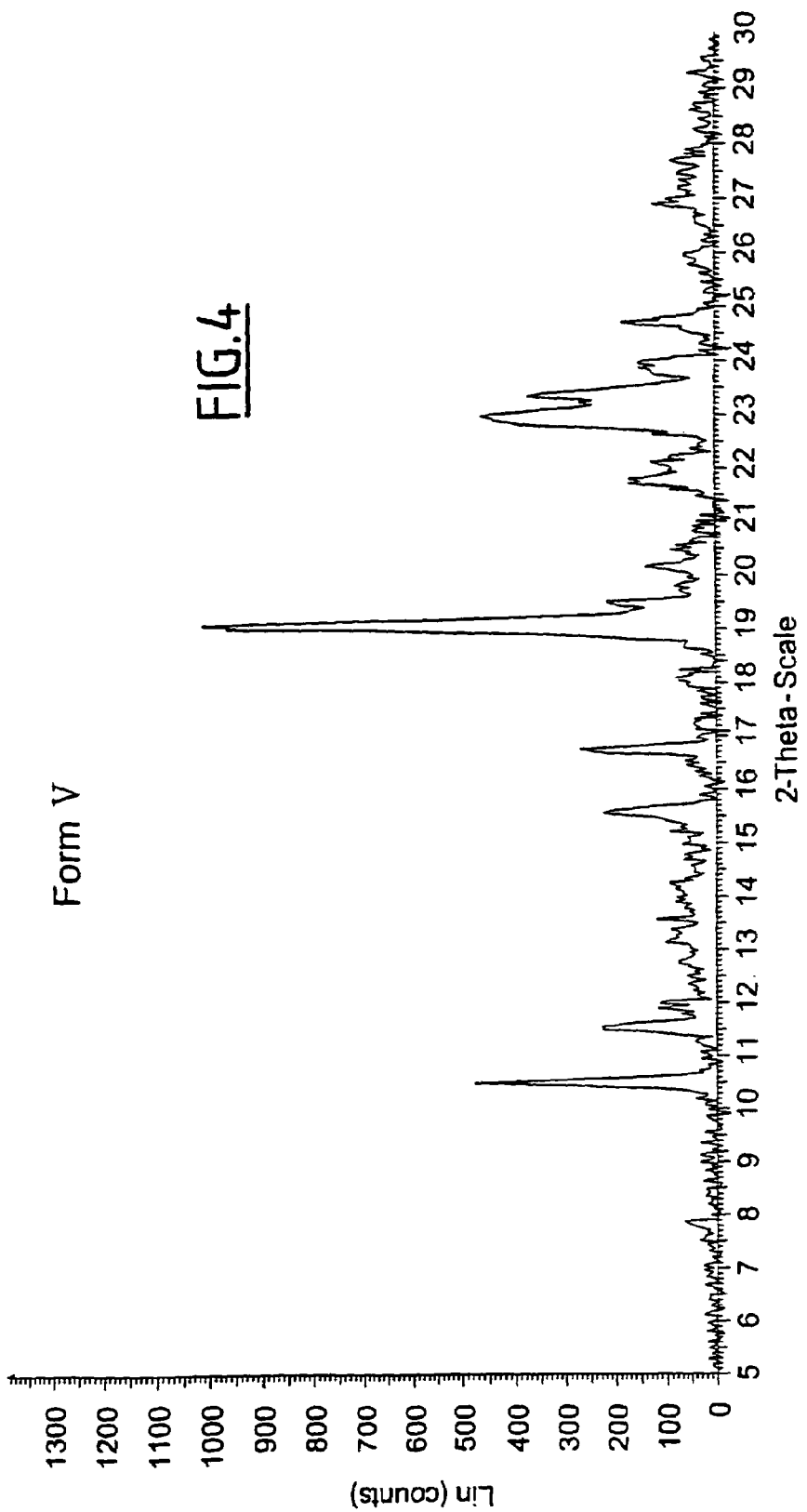
FIG. 4 represents a powder X-ray diffraction pattern of CRL 40476 form V.

The present invention also provides CRL 40476 form V (FIG. 4).

CRL 40476 form V produces the following powder X-ray diffraction pattern, wherein d represents interplanar spacing and $I/I_0$ the relative intensity:

| 2 Theta (degrees) | d (Å) | I/I₀ (%) |
|---|---|---|
| 7.77 | 11.4 | 14 |
| 10.48 | 8.44 | 49 |
| 11.52 | 7.67 | 35 |
| 11.94 | 7.40 | 28 |
| 13.30 | 6.65 | 29 |
| 14.19 | 6.24 | 31 |
| 15.59 | 5.68 | 43 |
| 16.44 | 5.39 | 31 |
| 16.76 | 5.29 | 47 |
| 18.05 | 4.91 | 33 |
| 19.09 | 4.64 | 100 |
| 19.46 | 4.56 | 42 |
| 20.16 | 4.40 | 38 |
| 20.48 | 4.33 | 34 |
| 21.80 | 4.07 | 39 |
| 22.11 | 4.02 | 35 |
| 22.97 | 3.87 | 58 |
| 23.38 | 3.80 | 51 |
| 23.92 | 3.72 | 35 |
| 24.74 | 3.60 | 35 |
| 26.00 | 3.424 | 24 |
| 26.92 | 3.309 | 28 |

The interplanar d-spacings of 8.44, 5.68, 5.29, 4.64, 4.56, 3.87, 3.80 (Å) are particularly characteristic.

Of these, the interplanar d-spacings of 8.44, 5.29, 4.64, 3.87, 3.80 (Å) are most characteristic.

Modafinil form V has a melting decomposition temperature of 159° C.

Modafinil Form VI (CRL 40476-[f VI])

Figure 5:
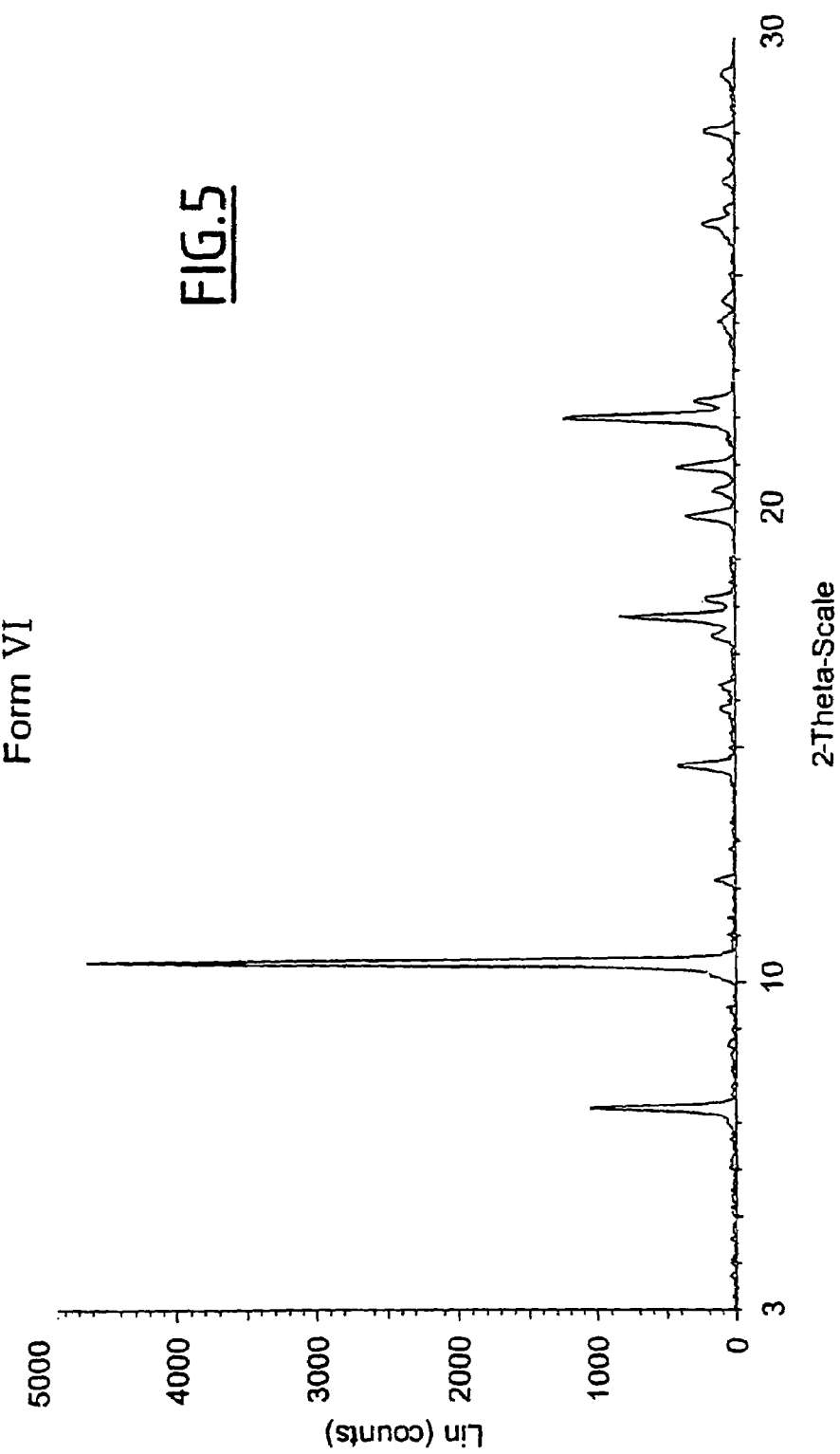
FIG. 5 represents a powder X-ray diffraction pattern of CRL 40476 form VI.

The present invention also provides CRL 40476 form VI (FIG. 5).

CRL 40476 form VI produces the following powder X-ray diffraction pattern, wherein d represents interplanar spacing and $I/I_0$ the relative intensity:

| 2 Theta (degrees) | d (Å) | I/I₀ (%) |
|---|---|---|
| 7.28 | 12.1 | 28 |
| 10.44 | 8.47 | 100 |
| 12.16 | 7.27 | 6 |
| 14.63 | 6.05 | 11 |
| 15.80 | 5.60 | 5 |
| 16.32 | 5.43 | 5 |
| 17.40 | 5.09 | 6 |
| 17.80 | 4.98 | 20 |
| 18.17 | 4.88 | 7 |
| 19.92 | 4.45 | 9 |
| 20.44 | 4.34 | 5 |
| 20.97 | 4.23 | 11 |
| 21.55 | 4.12 | 3 |
| 22.02 | 4.03 | 28 |
| 22.35 | 3.98 | 8 |
| 23.57 | 3.77 | 2 |
| 24.05 | 3.70 | 4 |
| 24.49 | 3.63 | 3 |
| 26.09 | 3.412 | 7 |
| 26.44 | 3.368 | 3 |
| 26.99 | 3.301 | 3 |
| 27.46 | 3.24 | 3 |
| 28.04 | 3.179 | 6 |
| 29.26 | 3.050 | 4 |

The interplanar d-spacings of 12.1, 8.47, 4.98, 4.23, 4.03 (Å) are particularly characteristic.

Of these, the interplanar d-spacings of 12.1, 8.47, 4.98, 4.03 (Å) are the most characteristic.

Modafinil form (VI) has a melting decomposition temperature of 159° C.

Figure 13:
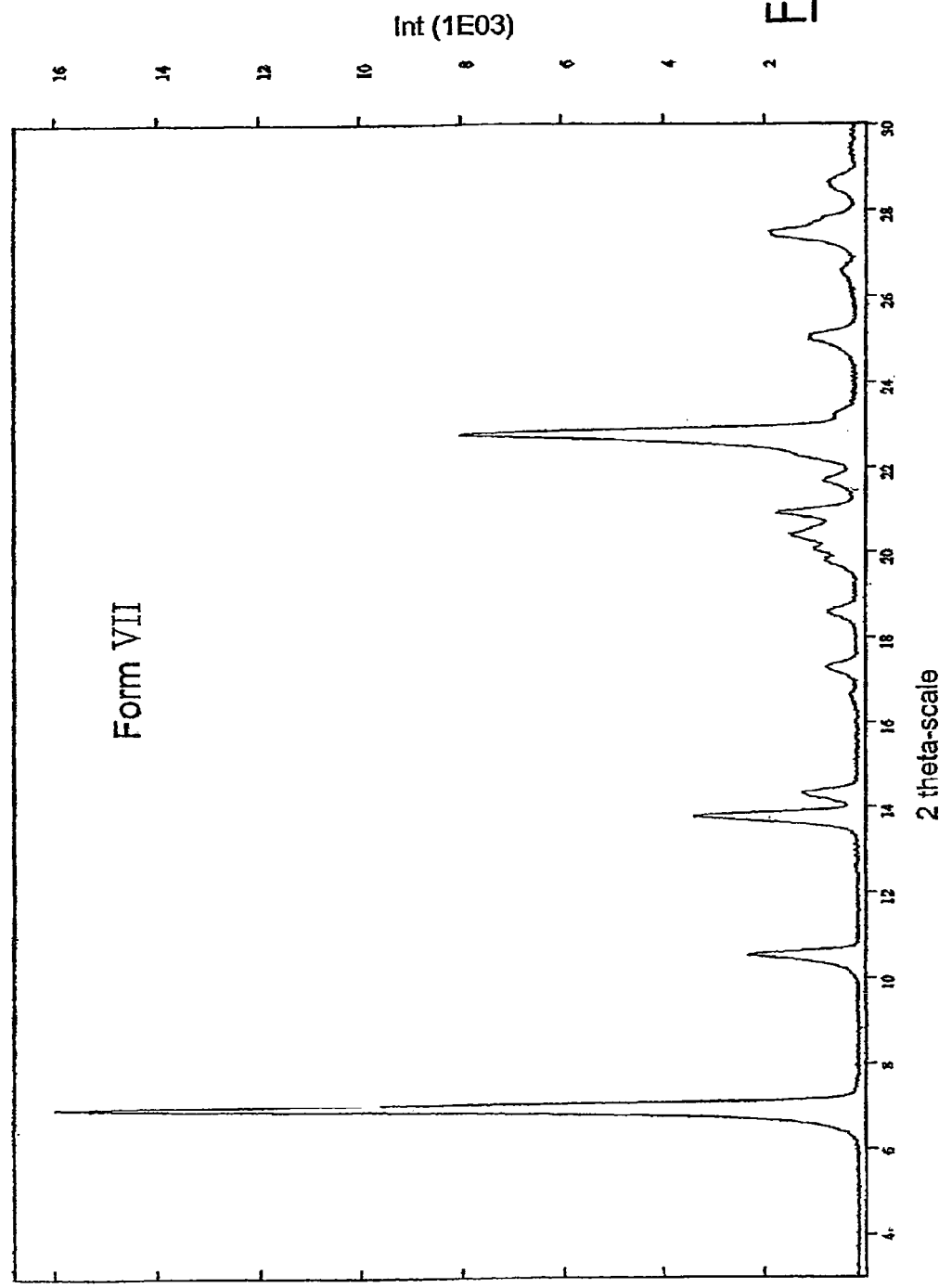
FIG. 13 represents a powder X-ray diffraction pattern of CRL 40476 form VII.

The present invention also provides CRL form VII (FIG. 13).

CRL form VII produces the following powder X-ray diffraction pattern, wherein d represents interplanar spacing and $I/I_0$ the relative intensity.

| 2 Theta (degrees) | d (Å) | I/Io (%) |
|---|---|---|
| 6.95 | 12.7 | 100 |
| 10.49 | 8.42 | 14 |
| 13.72 | 6.45 | 21 |
| 14.25 | 6.21 | 8 |
| 17.30 | 5.12 | 4 |
| 18.68 | 4.75 | 4 |
| 19.85 | 4.47 | 4 |
| 20.11 | 4.41 | 6 |
| 20.48 | 4.33 | 6 |
| 21.01 | 4.23 | 10 |
| 21.73 | 4.09 | 5 |
| 22.72 | 3.91 | 50 |

The interplanar d-spacings of 12.7, 8.42, 6.45, 4.23, 3.91 Å, are particularly characteristic.

Of these, the interplanar d-spacing of 12.7, 6.45 and 3.91 are most characteristic.

Modafinil form VII has a melting decomposition temperature of 158° C.

Novel Solvates of Modafinil

In addition to the identification of four novel polymorphic forms of modafinil, the present invention also provides an acetonitrile solvate of modafinil.

The present invention also provides solid solutions of modafinil corresponding to the general formula defined as:

Modafinil—[Tetrahydrofuran$_x$-Chloroform$_y$-Dioxane$_z$]

where x, y and z are defined by:

$$\begin{bmatrix} 0 \leq x \leq 1 \\ 0 \leq y \leq 1 \\ 0 \leq z \leq 1 \\ x + y + z = 1 \end{bmatrix}$$

From a thermodynamic point of view, these solid solutions constitute a single phase whatever the values of x. y and z.

Hereafter, the solid solutions of modafinil are referred to as modafinil solvate solid solution.

"Solvate" means an organised structure with an original crystal lattice, involving both solute and solvent molecules. The solvates of this invention are true solvates having a fixed ratio of about 1 solvent molecule per molecule of modafinil. The solvates of this invention are particularly useful as intermediates for subsequent reactions, for preparation of different polymorphs of modafinil and particularly to obtain forms that are not easily accessible by a direct crystallization in particular with good yields, namely forms V and VI.

The following tables represent powder X-ray diffraction patterns for the novel modafinil solvates.

Figure 6:
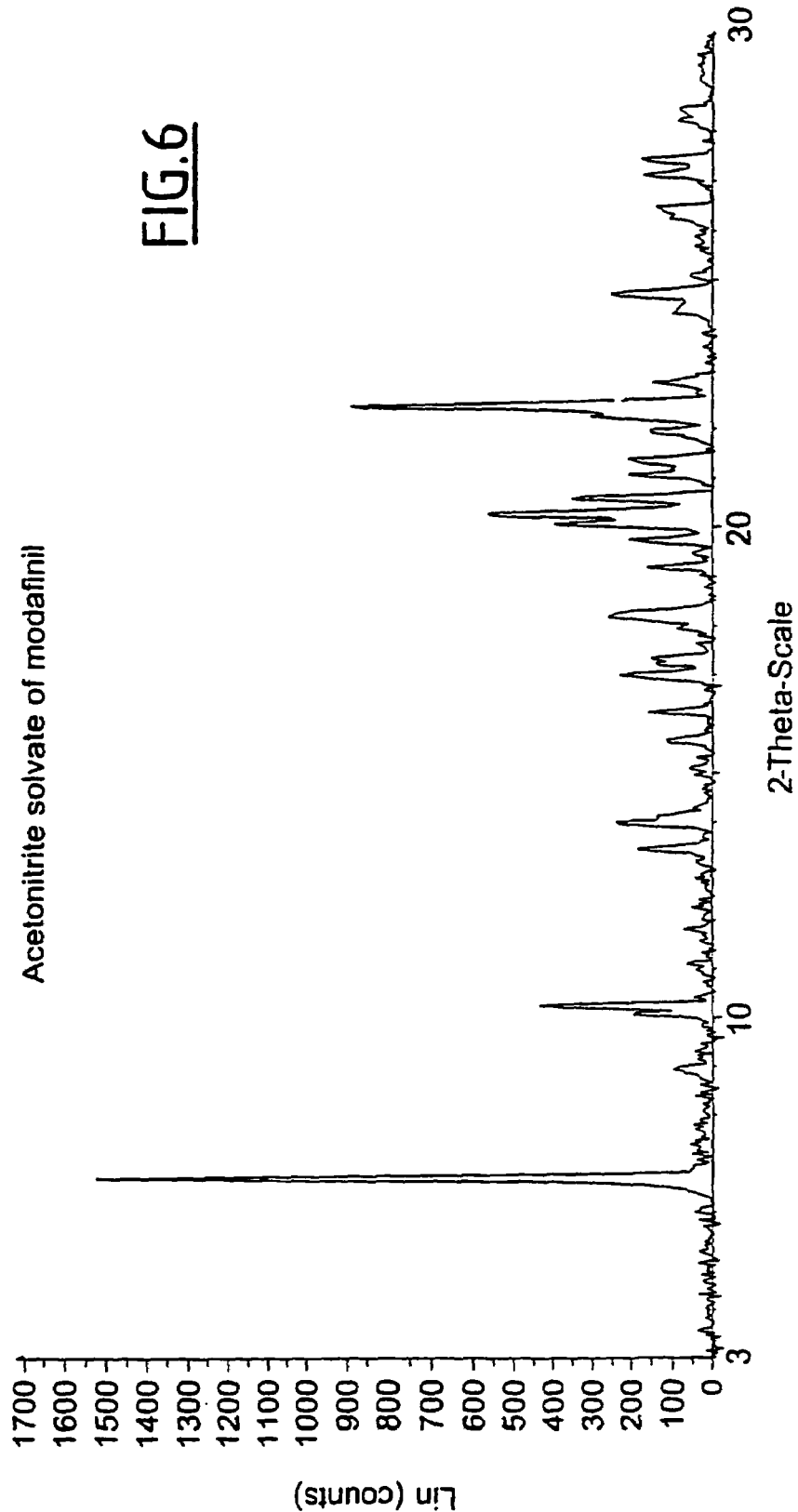
FIG. 6 represents a powder X-ray diffraction pattern of acetonitrile solvate of modafinil.

The acetonitrile modafinil solvate (FIG. 6) produces the following powder X-ray diffraction pattern, wherein d represents interplanar spacing and I/I$_0$ the relative intensity:

| 2 Theta (degrees) | d (Å) | I/I$_0$ (%) |
|---|---|---|
| 6.67 | 13.3 | 100 |
| 8.90 | 9.93 | 18 |
| 10.25 | 8.62 | 37 |
| 11.073 | 7.98 | 15 |
| 11.78 | 7.50 | 15 |
| 12.87 | 6.87 | 13 |
| 13.45 | 6.58 | 21 |
| 13.98 | 6.33 | 24 |
| 15.08 | 5.87 | 12 |
| 15.66 | 5.65 | 15 |
| 16.25 | 5.45 | 18 |
| 16.97 | 5.22 | 22 |
| 17.31 | 5.12 | 17 |
| 18.22 | 4.87 | 23 |
| 19.21 | 4.62 | 17 |
| 19.73 | 4.50 | 20 |
| 20.09 | 4.42 | 31 |
| 20.31 | 4.37 | 40 |
| 20.62 | 4.30 | 28 |
| 21.11 | 4.21 | 20 |
| 21.38 | 4.15 | 20 |
| 21.93 | 4.05 | 16 |
| 22.52 | 3.95 | 59 |
| 22.94 | 3.87 | 15 |
| 24.41 | 3.64 | 11 |
| 24.75 | 3.59 | 20 |
| 25.14 | 3.54 | 8 |
| 25.84 | 3.445 | 7 |
| 26.44 | 3.368 | 12 |
| 27.18 | 3.278 | 15 |
| 27.48 | 3.243 | 15 |
| 28.28 | 3.153 | 9 |
| 29.08 | 3.068 | 6 |

The interplanar d-spacings of 13.3, 8.62, 4.42, 4.37, 3.95 (Å) are particularly characteristic.

Figure 7:
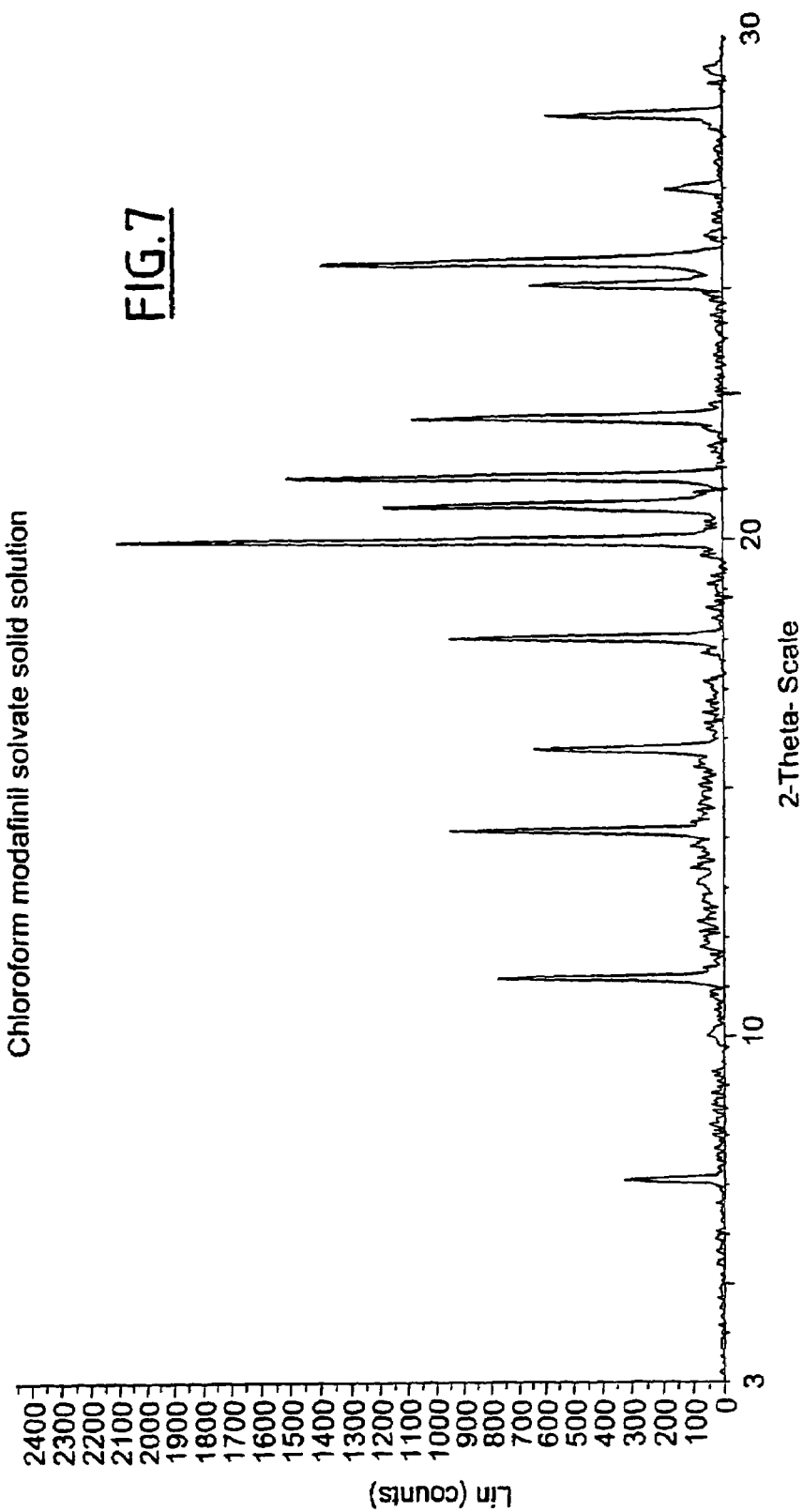
FIG. 7 represents a powder X-ray diffraction pattern of chloroform solvate solid solution of modafinil.

A chloroform modafinil solvate solid solution (where y=1) (FIG. 7) produces the following powder X-ray diffraction pattern, wherein d represents interplanar spacing and I/I$_0$ the relative intensity:

| 2 Theta (degrees) | d (Å) | I/I$_0$ (%) |
|---|---|---|
| 7.07 | 12.5 | 18 |
| 11.18 | 7.91 | 42 |
| 14.12 | 6.27 | 53 |
| 15.77 | 5.61 | 41 |
| 18.02 | 4.92 | 53 |
| 19.97 | 4.44 | 100 |
| 20.71 | 4.29 | 62 |
| 21.24 | 4.18 | 75 |
| 22.44 | 3.96 | 57 |
| 25.13 | 3.54 | 37 |
| 25.55 | 3.484 | 67 |
| 27.04 | 3.294 | 18 |
| 28.44 | 3.136 | 33 |
| 29.34 | 3.041 | 11 |

The interplanar d-spacings of 6.27, 4.92, 4.44, 4.29, 4.18, 3.96, 3.484 (Å) are particularly characteristic.

Figure 8:
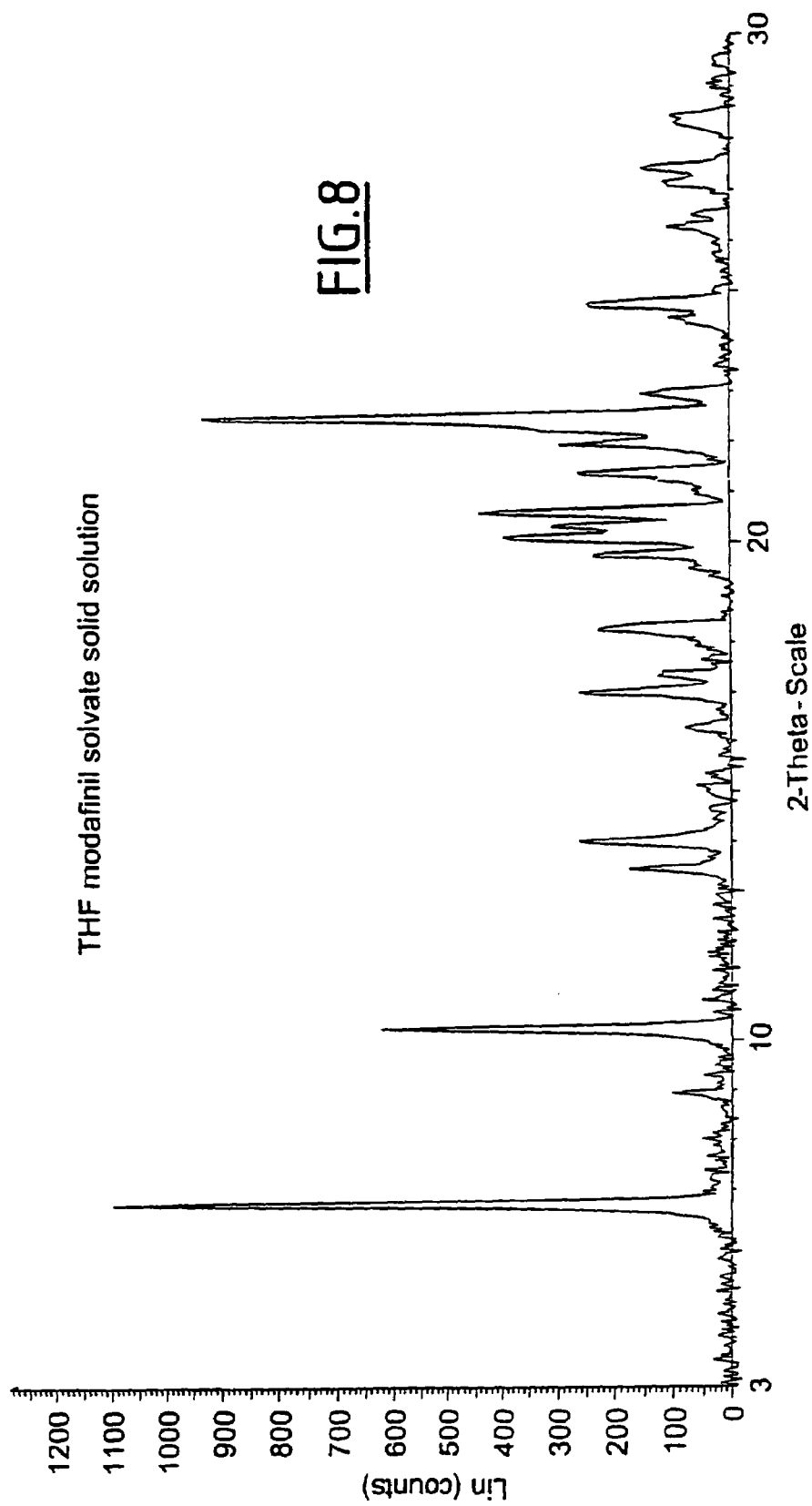
FIG. 8 represents a powder X-ray diffraction pattern of tetrahydrofuran solvate solid solution of modafinil.

A tetrahydrofuran modafinil solvate solid solution (where x=1) (FIG. 8) produces the following powder X-ray diffraction pattern, wherein d represents interplanar spacing and I/I$_0$ the relative intensity:

| 2 Theta (degrees) | d (Å) | I/I$_0$ (%) |
|---|---|---|
| 6.68 | 13.2 | 100 |
| 8.90 | 9.93 | 23 |
| 10.20 | 8.66 | 63 |
| 10.80 | 8.19 | 18 |
| 13.43 | 6.59 | 27 |
| 13.98 | 6.33 | 33 |
| 15.06 | 5.88 | 15 |
| 16.28 | 5.44 | 17 |
| 17.00 | 5.21 | 31 |
| 17.36 | 5.10 | 20 |
| 18.27 | 4.85 | 27 |
| 19.74 | 4.49 | 28 |
| 20.08 | 4.42 | 40 |
| 20.61 | 4.31 | 44 |
| 21.37 | 4.15 | 29 |
| 21.99 | 4.04 | 32 |
| 22.52 | 3.95 | 81 |
| 22.96 | 3.87 | 20 |
| 24.43 | 3.64 | 15 |
| 24.75 | 3.59 | 26 |
| 26.28 | 3.388 | 15 |
| 26.52 | 3.358 | 12 |
| 27.13 | 3.285 | 15 |
| 27.44 | 3.248 | 18 |
| 28.40 | 3.140 | 14 |
| 29.09 | 3.067 | 9 |
| 29.54 | 3.022 | 8 |

The interplanar d-spacings of 13.2, 8.66, 6.33, 4.31, 3.95 (Å) are particularly characteristic.

Figure 9:
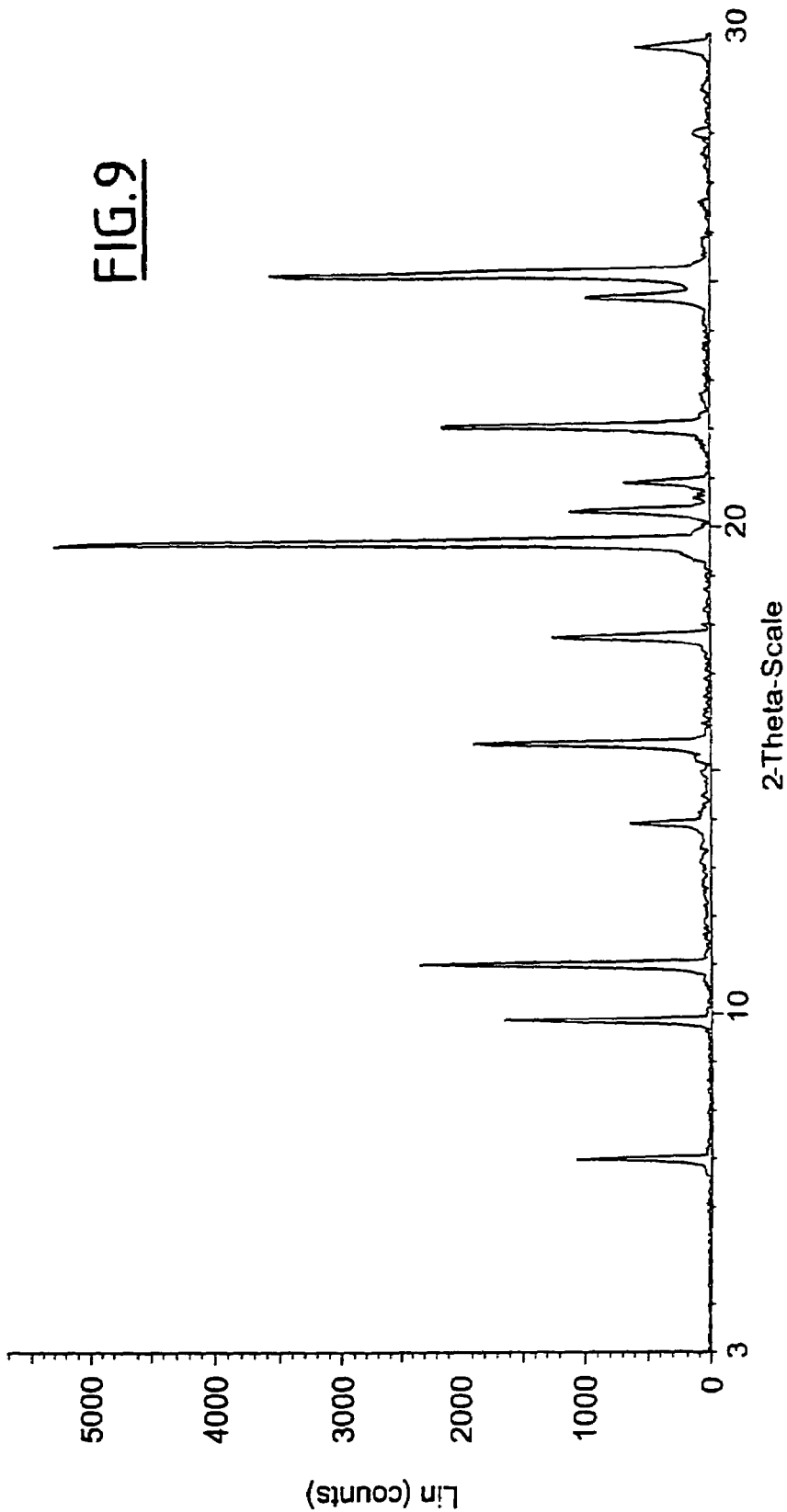
FIG. 9 represents a powder X-ray diffraction pattern of dioxane solvate solid solution of modafinil.

A dioxane modafinil solvate solid solution (where z=1) (FIG. 9) produces the following powder X-ray diffraction pattern, wherein d represents interplanar spacing and I/I$_0$ the relative intensity:

| 2 Theta (degrees) | d (Å) | I/I$_0$ (%) |
|---|---|---|
| 6.95 | 12.7 | 21 |
| 9.80 | 9.02 | 32 |
| 11.00 | 8.03 | 46 |
| 13.89 | 6.37 | 18 |
| 15.57 | 5.69 | 40 |
| 17.73 | 5.00 | 29 |
| 19.72 | 4.50 | 100 |
| 20.34 | 4.36 | 26 |
| 20.92 | 4.24 | 19 |
| 22.08 | 4.02 | 44 |
| 24.68 | 3.61 | 22 |
| 25.16 | 3.54 | 68 |
| 28.02 | 3.181 | 7 |
| 29.74 | 3.002 | 15 |

The interplanar d-spacings of 8.03, 5.69, 4.50, 4.02, 3.54 (Å) are particularly characteristic.

For modafinil solvate solid solutions with intermediate values of x, y and z. both interplanar spacings and relative intensities of X-ray diffraction patterns may vary between the above extreme situations, namely x=1 or y=1 or z=1.

Figure 10:
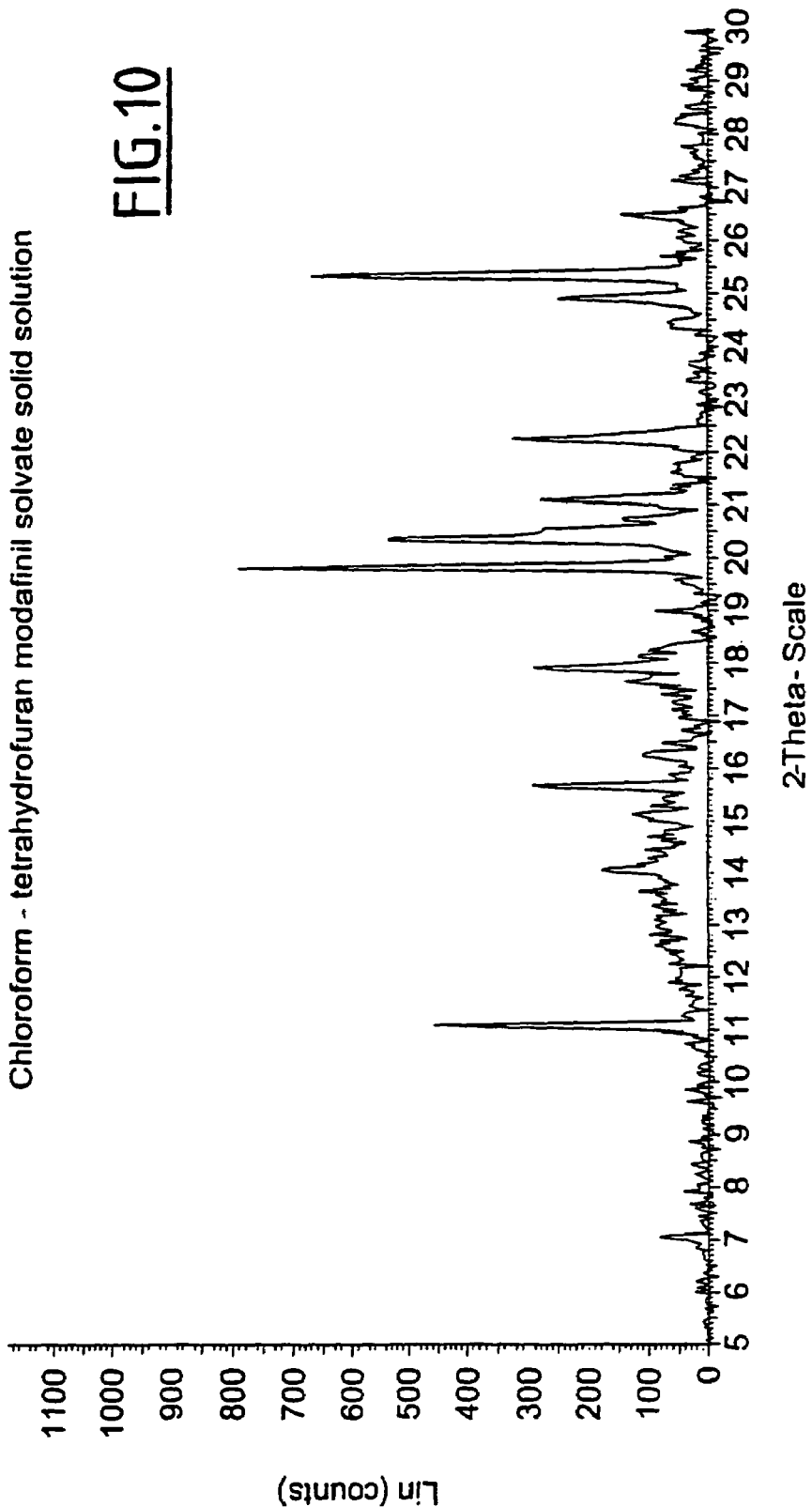
FIG. 10 represents a powder X-ray diffraction pattern of chloroform-tetrahydrofuran solvate solid solution of modafinil.

Examples of such variations are given below:

A chloroform-tetrahydrofuran modafinil solvate solid solution [where x+y=1 and prepared from a 1/1 (v/v) chloroform–tetrahydrofuran solution] (FIG. 10), produces the following powder X-ray diffraction pattern. wherein d represents interplanar spacing and I/I$_0$ the relative intensity:

| 2 Theta (degrees) | d (Å) | I/I$_0$ (%) |
|---|---|---|
| 6.99 | 12.6 | 18 |
| 11.08 | 7.98 | 59 |
| 14.08 | 6.29 | 44 |
| 15.11 | 5.86 | 42 |
| 15.67 | 5.65 | 57 |
| 16.26 | 5.45 | 42 |
| 17.68 | 5.01 | 45 |
| 17.91 | 4.95 | 58 |
| 18.96 | 4.68 | 40 |
| 19.84 | 4.47 | 100 |
| 20.40 | 4.35 | 78 |
| 21.11 | 4.21 | 56 |
| 21.72 | 4.09 | 35 |
| 22.26 | 3.99 | 58 |
| 24.45 | 3.64 | 33 |
| 24.94 | 3.57 | 48 |
| 25.39 | 3.51 | 83 |
| 26.49 | 3.361 | 36 |
| 27.18 | 3.277 | 28 |
| 28.30 | 3.150 | 26 |

Figure 11:
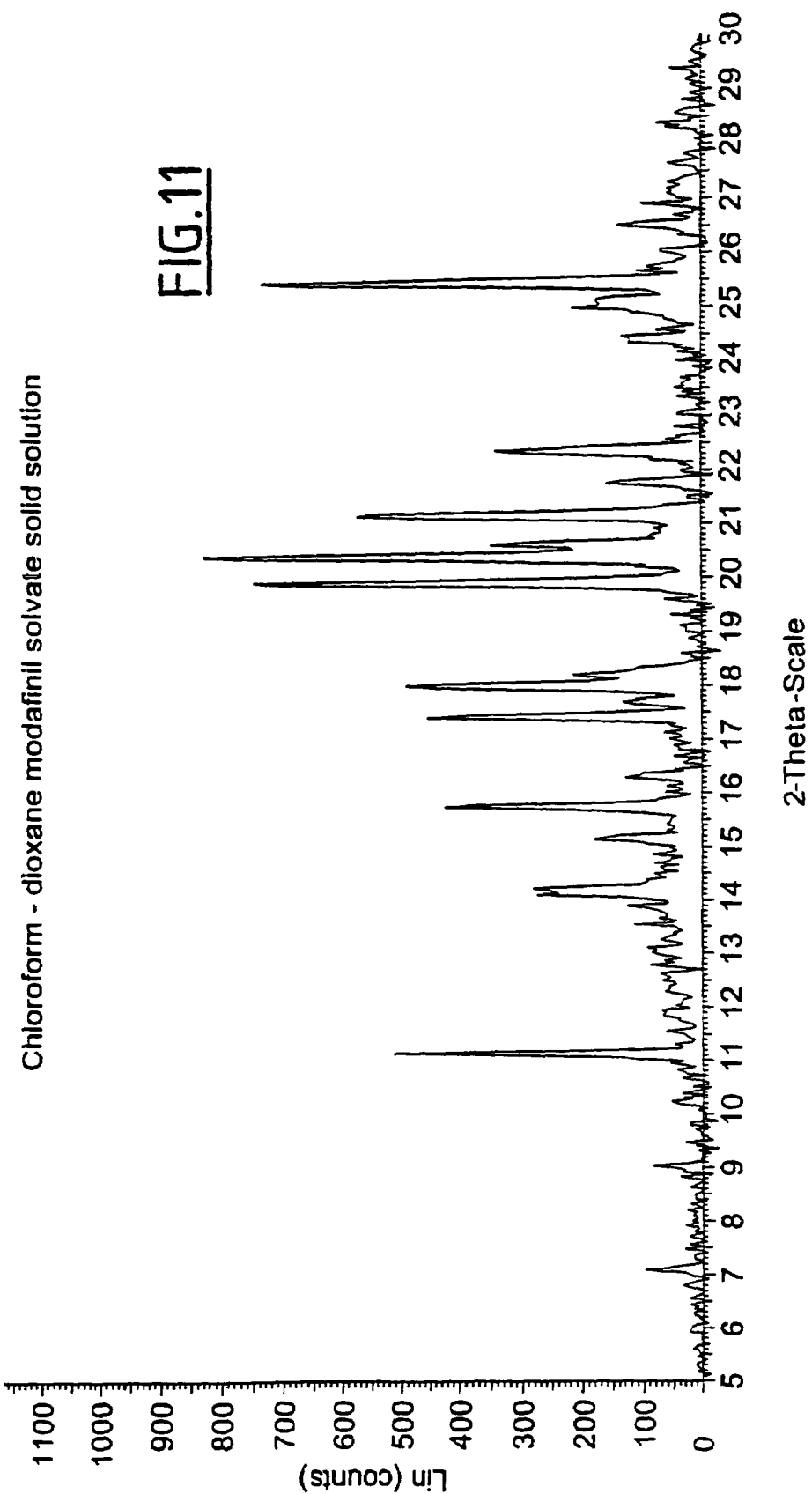
FIG. 11 represents a powder X-ray diffraction pattern of chloroform-dioxane solvate of solid solution modafinil.

A chloroform-dioxane modafinil solvate solid solution [where y+z=1 and prepared from a 1/1 (v/v) chloroform–dioxane solution] (FIG. 11), produces the following powder X-ray diffraction pattern, wherein d represents interplanar spacing and I/I$_0$ the relative intensity:

| 2 Theta (degrees) | d (Å) | I/I$_0$ (%) |
|---|---|---|
| 7.06 | 12.5 | 19 |
| 8.99 | 9.82 | 21 |
| 10.20 | 8.67 | 21 |
| 11.08 | 7.97 | 63 |
| 11.86 | 7.45 | 28 |
| 13.04 | 6.78 | 34 |
| 14.15 | 6.26 | 52 |
| 15.16 | 5.84 | 45 |
| 15.74 | 5.63 | 66 |
| 16.30 | 5.43 | 42 |
| 17.42 | 5.09 | 70 |
| 17.96 | 4.94 | 73 |
| 19.08 | 4.65 | 34 |
| 19.88 | 4.46 | 94 |
| 20.37 | 4.36 | 100 |
| 21.17 | 4.19 | 78 |
| 21.78 | 4.08 | 42 |
| 22.36 | 3.97 | 56 |
| 23.61 | 3.76 | 28 |
| 24.45 | 3.64 | 35 |
| 25.08 | 3.55 | 39 |
| 25.45 | 3.497 | 85 |
| 26.05 | 3.418 | 28 |
| 26.56 | 3.353 | 34 |
| 27.25 | 3.269 | 26 |
| 27.68 | 3.220 | 26 |
| 28.39 | 3.141 | 27 |

Methods for preparing CRL 40476 forms I, III, IV, V, VI and VII

This invention also provides efficient methods to prepare CRL 40476 forms I, III, IV, V, VI and VII.

Method for Preparing Mondafinil Polymorphs III, IV, V VI AND VII Via Solvates Formation In a first method of this invention, a modafinil polymorphic form can be prepared with high purity, according to a general procedure comprising the following steps:

i) preparing a modafinil solvate which can also be a modafinil solvate solid solution; and ii) desolvating the modafinil solvate to obtain a given polymorphic form.

"Desolvating" and "desolvation" mean the elimination of most or all solvent molecules, preferably greater than or equal to 90%, more preferably greater than or equal to 95%, most preferably greater than or equal to 99% from the solvate that leads to the conversion of the solvate into the polymorph.

Preparation of Modafinil Solvates

The modafinil solvates may be prepared by:

i) Dissolving any physical species of modafinil in a solvent preferably selected from the group consisting of acetonitrile, tetrahydrofuran, chloroform and dioxane or mixtures thereof, more preferably tetrahydrofuran, chloroform or dioxane as single solvents or as mixtures thereof; and ii) Crystallizing Modafinil Solvate From the Solution.

The temperature of the solution may preferably be from ambient temperature to 110° C., more preferably the reflux temperature at atmospheric pressure of the solvent or of the solvent mixtures selected. Preferably, the preparation is stirred up to complete dissolution.

The solvate of modafinil may be crystallized from the solution by conventional methods, including cooling or chilling, crystal seeding, and evaporation of a portion of the solution. A preferred embodiment comprises cooling slowly and evaporating a portion of the solution at 20° C., under atmospheric pressure. The crystals are preferably isolated by filtration.

A preferred embodiment of preparation of modafinil solvates comprises:

i) Heating the solvent or the solvent mixture under reflux then adding modafinil by fractions until saturation is reached (additionnal solvent may be added to ensure complete dissolution); and ii) Cooling the resulting solution, preferably slowly, to room temperature to obtain modafinil solvate, preferably modafinil solvate crystals (typically by leaving it at room temperature under atmospheric pressure).

Modafinil solvate crystals can be obtained after cooling and a slow evaporation of solvent. The crystals are preferably isolated by filtration.

Desolvation of Modafinil Solvate

The desolvabon conditions of this method constitute an important set of rules that determine the nature of modafinil polymorphic forms. Thus, for example, a chloroform solvate can lead to different polymorphic forms, respectively to form III and form V, according to conditions of desolvation.

Generally, desolvation comprises drying the modafinil solvate by heating either under atmospheric or reduced pressure, or by first vacuum filtering and then heating under atmospheric or reduced pressure.

The heating temperature may vary based on pressure, desired rate of desolvation and desired polymorphic form. Conditions of desolvation will be described more in detail hereinafter for each polymorphic form III, IV, V and VI.

Method for Preparing Mondafinil Polymorphs I, III, IV AND VII Via Direct Crystallization In a second method of this invention, a modafinil polymorphic form can be prepared according to a general procedure comprising the following steps:

i) dissolving any physical species of modafinil in a solvent, preferably in chloroform, tetrahydrofuran, acetonitrile, acetone and methanol;

ii) crystallizing the modafinil polymorphic form from the solvent; and iii) separating the modafinil polymorphic form from the solvent.

In this method, the nature of the solvent selected and the conditions of crystallization selected can be used to direct the preparation of any of the polymorphic forms. Crystallization solvents and conditions will be disclosed hereinafter for each modafinil form, respectively I, III, IV and VII obtained according to this method.

A preferred embodiment comprises dissolving modafinil by heating the solvent under reflux then adding modafinil by fractions until saturation is reached. Additional solvent may be added to ensure complete dissolution.

The modafinil polymorphic form may be crystallized from the solution either by conventional methods, including cooling or chilling, crystal seeding, evaporation of a portion of the solution, or by precipitation, preferably by addition of water.

A preferred embodiment comprises cooling the solution rapidly by standard cooling methods. Another preferred embodiment comprises precipitating the crystals by adding water, preferably cold water.

The modafinil polymorphic form may be isolated by conventional methods including filtration and centrifugation.

Modafinil form I was identified as the thermodynamic form (at room temperature). Form I is obtained via crystallization, preferably under atmospheric pressure, at room temperature.

It will be understood that the concentration of modafinil is not a critical factor in the preparation of the solvate or in the direct preparation of polymorphs by crystallization. However, it is particularly convenient to use a concentration of modafinil close to the saturation value in the respective solvent.

Polymorphs may be prepared with a specific surface area or a defined particle size. The specific surface area may vary with crystallization conditions and drying conditions, in the method via direct crystallization (in particular with modafinil concentration, seeding, and cooling) and with desolvation conditions, in the method via solvates formation.

Methods for Preparing Form I (CRL 40476-[f I])

Form I may be prepared with high purity by the method via direct crystallization at room temperature or by using control cooling comprising the steps:

i) dissolving modafinil in a solvent, preferably in a solvent selected from the group consisting of methanol, 2-methoxyethanol, ethanol, acetone, N,N-dimethylformamide, or in a mixture of water with one of these solvents;

ii) crystallizing by evaporating a portion of this solution preferably at a temperature in the range of 20° C.-120° C. under atmospheric pressure, more preferably at about 20° C. with a reaction time of about 10-20 days, or crystallizing by regular controlled cooling of the previous solution, below 20° C., preferably below −10° C.; and iii) separating modafinil form I from the solvent.

Form I being the most stable form at 20° C., it may also be prepared from any polymorphic form or solvate, by a long slurrying in methanol, 2-methoxyethanol, ethanol, acetone, N,N-dimethylformamide, or in a mixture of water with one of these solvents, with or without previous seeding with form I, at room temperature, under vigorous stirring.

"A long slurrying" is understood as a sufficient time to reach equilibrium conditions.

Methods for Preparing Form III (CRL 40476-[f III])

Form III can be prepared with high purity via solvates formation method comprising:

i) preparing a modafinil solvate from a solvent selected from the group consisting of dioxane, chloroform, tetrahydrofuran, or in a mixture thereof, and acetonitrile; and ii) desolvating the modafinil solvate to obtain modafinil form III by heating the resulting modafinil solvate.

In a preferred embodiment of this method, step ii) consists in heating the previously obtained crystals at a temperature preferably in the range of 110° C.-140° C. under atmospheric pressure, more preferably at 110° C., during 12 hours.

Form III may be prepared with high purity via direct crystallization comprising the steps:

i) dissolving modafinil in a solvent selected from the group consisting of acetonitrile, chloroform, tetrahydrofuran and methanol;

ii) crystallizing modafinil from the solvent; and iii) separating the solvent to obtain modafinil form III.

In a preferred embodiment of this method, when solvents are acetonitrile, chloroform or tetrahydrofuran, step ii) comprises cooling rapidly, typically at a rate of −10° C./min, the previous solution down to 5° C.

When the selected solvent is methanol, step ii) may comprise either cooling the modafinil solution rapidly, typically with a cooling rate temperature in the range of −0.5° C./min to −1° C./min, or in precipitating modafinil by adding, under stirring, from one to nine volumes of water to the methanol solution to obtain a 50/50 to 10/90 (w/w) final volume of methanol/water mixture. The above cooling rate should be high enough to avoid the formation of the thermodynamic form I.

In a preferred embodiment of step ii), modafinil is precipitated by adding, under stirring, one volume of water to 1.25 volumes of methanol to obtain a 50/50 (w/w) final volume of methanol/water mixture.

Preferably, step iii) comprises filtering and drying the resulting crystals.

Form III may also be prepared with high purity from form V, form VI or from any modafinil solvate by:

i) heating modafinil form V or form VI or modafinil solvate to a temperature from 110° C. to 130° C., more preferably at 130° C.; and ii) cooling to room temperature for a sufficient time to complete the conversion.

In a preferred embodiment, modafinil form III has a specific surface area in the range of 0.3 to 1.0 m$^2$/g, preferably of 0.5 m$^2$/g.

Methods for Preparing Form IV (CRL 40476-[f IV])

Form IV may be prepared with high purity via solvates formation method comprising:

i) preparing a modafinil solvate from a solvent selected from the group consisting of tetrahydrofuran, chloroform, dioxane and a mixture thereof; and ii) desolvating the modafinil solvate to obtain modafinil form IV.

A preferred temperature of desolvation is in the range of 20° C. to 30° C. under atmospheric pressure, more preferably at about 20° C. for a time of about one month.

In a preferred embodiment of this method, step ii) comprises allowing desolvation of the previously obtained solvates by slow evaporation of solvent at about 20° C. over several weeks.

Form IV may be prepared with high purity via direct crystallization comprising the steps:

i) dissolving modafinil in methanol;

ii) crystallizing modafinil from the solvent, by adding a volume of water, preferably in the proportion in the range of 50/50 to 90/10 (v/v) to the methanol solution without stirring; and iii) separating the mother liquor to obtain modafinil form IV.

In a preferred embodiment of this method, step ii) comprises pouring this solution into cold water without stirring and step iii) comprises filtering the resulting mixture on a large surface area filter to eliminate most residual methanol, then drying the isolated solid at 80° C. in a ventilated oven.

In a preferred embodiment, modafinil form IV is obtained with a specific surface area in the range of 0.2-1.0 m$^2$/g, preferably of 0.7 m$^2$/g.

Methods for Preparing Form V (CRL 40476-[f V])

Form V may be prepared with high purity via solvates formation comprising:

i) preparing a solvate of modafinil from a solvent selected from the group consisting of tetrahydrofuran, dioxane and chloroform, or a mixture thereof; and ii) desolvating the solvate of modafinil to obtain modafinil form V, preferably by heating the modafinil solvate at an appropriate heating temperature to obtain modafinil form V.

In the case of tetrahydrofuran, a preferred heating temperature for desolvation is from 40° C. to 70° C. under atmospheric pressure, more preferably from about 60° C. for a time of about 5 hours. A most preferred embodiment consists in filtering under vacuum and then heating the crystals to a temperature in the range of 40° C. to 70° C., preferably to 60° C. for a time of about 5 hours.

In the case of dioxane, a preferred heating temperature for desolvation is from 20° C. to 30° C. under atmospheric pressure, more preferably from about 20° C. for a time of about one week. A most preferred embodiment consists in filtering under vacuum and heating to a temperature in the range of 60° C.-90° C., preferably to about 90° C., for a time of about five hours.

In the case of chloroform, a preferred heating temperature for desolvation is from 60° C. to 90° C. under vacuum, more preferably at about 80° C. for a time of about 1 hour. A most preferred embodiment comprises filtering under vacuum and heating under atmospheric pressure, at a temperature in the range of 70° C.-100° C., preferably at about 90° C., for a time of about 5 hours.

In a preferred embodiment, modafinil form V is obtained with a specific surface area in the range of 2 to 14 m$^2$/g, preferably of 11 m$^2$/g.

Methods for Preparing Form VI (CRL 40476-[f VI])

Form VI can also be prepared with high purity via solvates formation method comprising:

i) preparing a modafinil solvate from acetonitrile; and ii) desolvating the modafinil solvate to obtain modafinil form VI.

A preferred desolvation temperature is from 10° C. to 30° C., more preferably at about 20° C., preferably for a time of about 3 days under atmospheric pressure or for a time of about 6 hours under reduced pressure.

Figure 12:
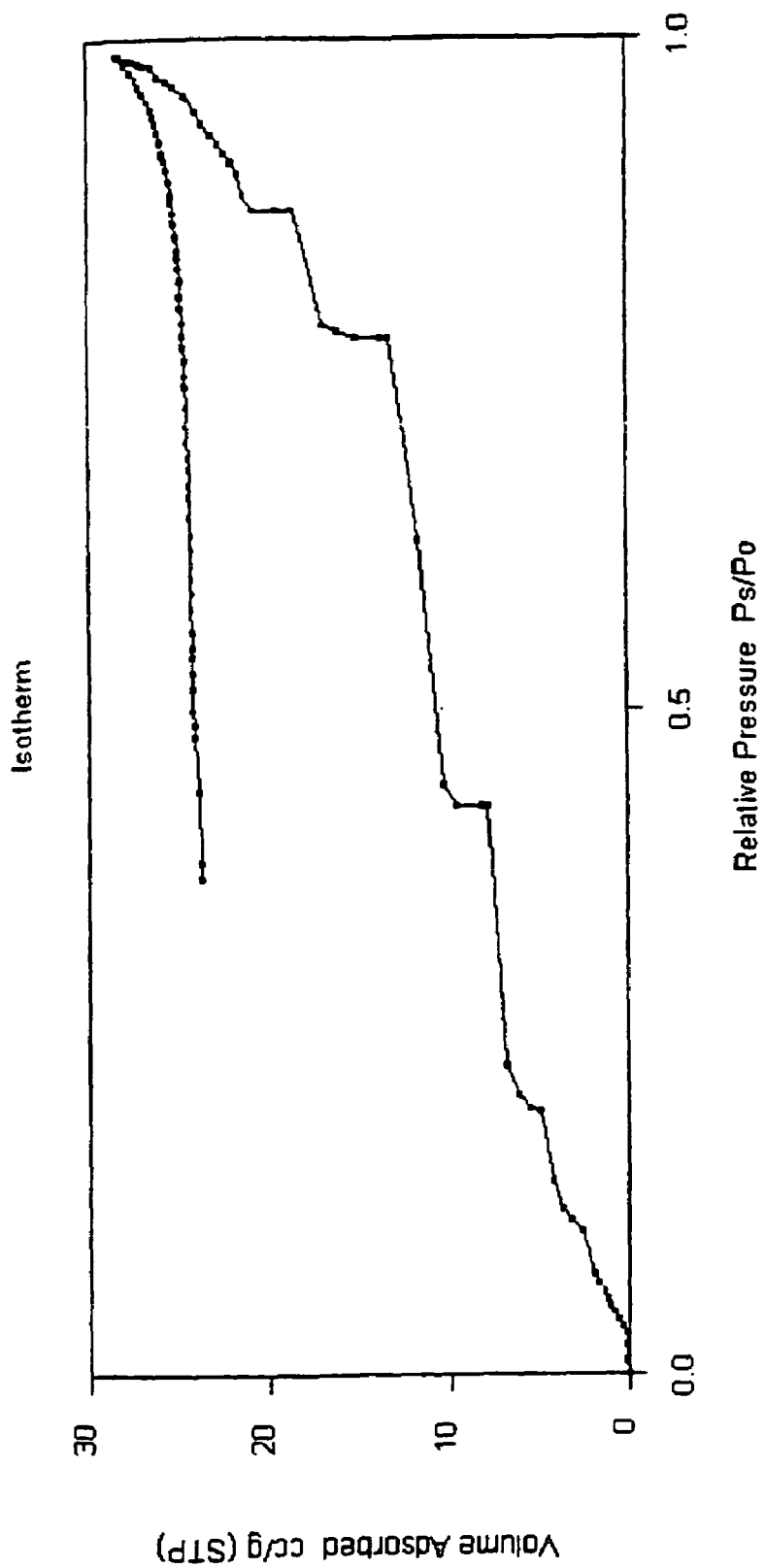
FIG. 12 represents the complete adsorption and desorption isotherm (Type VI) at 60° C. of form VI (CRL 40476-[f VI]).

In a preferred embodiment, modafinil form VI is obtained, with a specific behavior classified as Type VI according to Brunauer Elmett Teller classification, (FIG. 12).

Method for Preparing Form VII (CRL 40476-[f VII])

Form VII may be prepared with high purity via direct crystallization comprising the steps of:

i) dissolving modafinil in acetone;

ii) crystallizing modafinil from the solvent, by adding a volume of water in the range of 50/50 to 90/10 (v/v) based on the acetone solution without stirring; and iii) separating the solvent to obtain CRL 40476 form VII.

In a preferred embodiment of this method, the solution resulting from step i) is subsequently filtered on a glass filter in order to remove tiny insoluble particles.

In accordance with a preferred aspect of this method, step ii) comprises pouring the solution of step i), optionally filtered, into cold water without stirring.

Preferably, the obtained mixture is maintained without stirring at room temperature, i.e. at about 20° C., during a sufficient time to allow a substantial amount of modafinil to crystallize, for example for a time of about 12 hours.

Preferably, step iii) comprises filtering the mixture resulting from step ii) on a large surface area filter.

Pharmaceutical Compositions Containing Modafinil Forms III, IV, V, VI and VII

Modafinil forms III, IV, V, VI and VII may be formulated into a variety of pharmaceutical compositions and dosage forms.

The dosage form and composition depend upon the route of administration. Any route of administration may be contemplated, including oral route, mucosal route (e.g. ocular, intranasal, pulmonary, gastric, intestinal, rectal, vaginal, or urinary tract) or parenteral route (e.g. subcutaneous, intradermal, intramuscular, intravenous, or intraperitoneal).

Pharmaceutical compositions described herein are most preferably administered orally, preferably in pharmaceutical forms (drug delivery system) such as tablets, capsule, powder, pill, liquid/suspension or gelsuspension or emulsion, lyophillizate and all other different forms described in patents and applications mentioned herein, more preferably in the form of a tablet, capsule and liquid/suspension or gel/suspension. The administration vehicle may comprise one or more pharmaceutically acceptable carriers that is likely to ensure polymorphs stability (e.g. polymorph suspension in oil).

Pharmaceutical compositions of the present invention comprise modafinil forms III, IV, V, VI and VII optionally in mixture with each other or with one or more pharmaceutically acceptable excipients. Suitable excipients are, in particular, for oral administration, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). Suitable binders include for instance, povidone, copovidone, dextran, dextrin, cyclodextrin and derivatives such as hydroxypropylbetacyclodextrin. Sweeteners can be added, such as aspartam, saccharin, sodium cyclamate as well as flavoring agents. Suitable surfactants and emulsifiers are, in particular, polysorbate 20, 60, 80, sucroester (7-11-15), poloxamer 188, 407, PEG 300, 400, sorbitan stearate. Solubilisers can be added such as miglyol 810, 812, glycerides and derivatives, propyleneglycol. If desired, disintegrating agents can be added, such as the crosslinked polyvinyl pyrrolidone, cross carmellose sodium, or alginic acid or a salt thereof such as sodium alginate. Lubricants can also be added such as magnesium stearate, leucine, magnesium stearyl fumarate, is behenic acid and derivatives.

Pharmaceutical compositions of the present invention also may contain other modafinil crystalline forms including form I and/or other active or inactive ingredients in mixture with one or more modafinil forms III, IV, V, VI and VII.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The carrier may comprise agents that aid solubility in the body, absorption, flavor, color or texture of the vehicle or its contents. Topical administration via an epidermal patch or the like, or administration via direct injection of the drug, is also acceptable.

Unit dosage forms preferably may contain from about 5 mg to about 800 mg of modafinil, preferably from about 25 mg to about 400 mg, more preferably from about 50 mg to about 300 mg, most preferably from about 50 mg to 200 mg.

The doses of modafinil polymorphs used for the administration can be adapted as a function of various parameters, and in particular as a function of the mode of administration used, of the relevant pathology, of the polymorphic form used, or alternatively of the desired duration of treatment.

As demonstrated thereafter, compositions containing modafinil form IV can include modafinil in dosage levels inferior than those commonly used to obtain an equivalent therapeutic efficiency with form I. As a consequence, modafinil form IV, may advantageously replace modafinil form I to increase the oral bioavailability of modafinil without delaying or modifying the onset of therapeutic action of modafinil (on hypersomnolence states as in narcoleptic patients for example or in any other therapeutic indication). The crystalline form IV of modafinil described herein may be formulated into appropriate pharmaceutical compositions in replacement of form I. Using such pharmaceutical compositions, an equivalent therapeutic effect may be achieved at lower dosages, thereby increasing the benefit/risk ratio of modafinil by reducing for example the modafinil-monooxygenases (cyt P450) interactions, such interactions being sources of potential deleterious or cumbersome drug-drug interactions.

Preferably, compositions containing modafinil form IV are characterized by a dosage level inferior by about 5% to about 50%, preferably by about 10% to about 30%, more preferably by about 15% to about 25%, most preferably by about 20% as compared to those of form I commonly used for the same purpose.

As also demonstrated hereafter, compositions comprising modafinil form V reduce the delay of wake-promoting activity of modafinil. As a consequence, by replacing modafinil racemate form I by modafinil racemate form V, the delay of therapeutic action of modafinil (on hypersomnolence states as in narcoleptic patients for example or in any other therapeutic indication) is reduced. The crystalline form V of modafinil described herein may be formulated into appropriate pharmaceutical compositions as described herein in replacement of form I. The use of such form of modafinil with reduced delay of action is of interest in all pathological situations where it is important to restore rapidly a normal vigilance level (for example, narcoleptic patients particularly when hypersomnolence episode appears during social or professional life, fatigue syndrome, shift work, jet lag etc.).

Methods of Use

Modafinil forms III, IV, V, VI and VII are useful for treating a variety of diseases and disorders, including:

sleep disorders such as:
- hypersomnia, including idiopathic hypersomnia and hypersomnia in cancer patients that are administrated with morphinic analgesics to relieve severe pain,
- sleep apneas, excessive sleepiness associated with a disease, obstructive sleep apnea,
- narcolepsy: sleepiness, excessive sleepiness, excessive sleepiness associated with narcolepsy;

central nervous system disorders such as Parkinson's disease;

protecting cerebral tissue from ischemia;

vigilance disorders including:
- vigilance disorders associated with Steinert's disease,
- attention disorders, e.g. linked to hyperactivity (ADHD);

tiredness and fatigue, particularly tiredness and fatigue associated with multiple sclerosis and other degenerative diseases;

depression, depressive mood linked to weak sunlight (sundowning);

schizophrenia;

shift work, time lag including jet lag;

food behaviour disorders, wherein modafinil acts as an appetite stimulant;

as well as stimulating cognitive functions at low doses.

Because of its improved global resorption yield, modafinil form IV is particularly useful to increase the ratio benefit/risk of the drug, for example by reducing modafinil quantity that interacts with hepatic monooxygenases (cyt P450).

Accordingly, the present invention provides a method for treating a human including a patient, suffering from a disease or a disorder known to be responsive to the administration of modafinil, by administering to said human, an effective amount of modafinil form IV which is lower by about 5% to about 50%, preferably lower by about 10% to about 30%, more preferably lower by about 15% to about 25%, most preferably lower by about 20%, than the corresponding amount of modafinil form I, that is to say, an amount of modafinil form I commonly used for the treatment of such diseases or disorders.

Preferably, this method involves treating an adult human with a daily amount of modafinil form IV in the range of 150 mg to 250 mg, instead of the current daily dose which is in the range of 200 mg to 300 mg.

More preferably, the daily dose of form IV is from 2.3 mg to 3.9 mg per kg, (normalization based on a mean body weight close to 65 kg).

For example, for the treatment of a patient suffering from diseases and disorders as described above, the most relevant daily amount of form IV can be from 2.5 mg to 3.5 mg per kg.

Modafinil form V is particularly recommended in treatment of hypovigilance states and stimulation of cognitive functions, by substantially reducing the time period needed for therapeutic action of modafinil, as soon as a faster response than that gained with form I is requested.

Accordingly, the present invention provides a method for increasing vigilance in a human, after a shortened time period following the administration, by administering to said human an effective amount of modafinil form V.

Preferably, form V has been shown to be efficient as soon as 2.2 hours to 2.5 hours, and even preferably as soon as 1 hour to 1.5 hours, after oral administration, corresponding to a shortening onset of action as compared to form I, and more importantly corresponding to a 50% reduction of the time needed for answer onset.

The invention also provides a method for obtaining more rapidly a therapeutically efficient concentration in blood of a human by administering to said human an effective amount of modafinil form V.

Overall, form V administration is devoted to all situations where a very rapid wakening effect is needed without any detrimental effect on modafinil clearance.

Preferably, said efficient concentration is obtained within about less than 1 hour after administration.

An "effective amount" is an amount that is able to reduce or eliminate the symptoms of diseases and disorders, including: sleep disorders such as hypersomnia, including idiopathic hypersomnia and hypersomnia in cancer patients that are administered with morphinic analgesics to relieve severe pain, sleep apneas, excessive sleepiness associated with a disease, obstructive sleep apnea, narcolepsy: sleepiness, excessive sleepiness, excessive sleepiness associated with narcolepsy ; central nervous system disorders such as Parkinson's disease; for protecting cerebral tissue from ischemia ; vigilance disorders including vigilance disorders associated with Steinert's disease, attention disorders, e.g. linked to hyperactivity (ADHD); tiredness and fatigue, particularly those associated with multiple sclerosis and other neurodegenerative diseases; depression, depressive mood linked to weak sunlight (sundowning); schizophrenia; shift work, time lag including jet lag; as well as food behaviour disorders, wherein modafinil acts as an appetite stimulant.

A "therapeutically efficient concentration" is understood as the concentration of modafinil that must be available in blood of a human, including a patient, for the effective and relevant treatment of a human suffering from diseases and disorders, including: sleep disorders such as hypersomnia, including idiopathic hypersomnia and hypersomnia in cancer patients that are administered with morphinic analgesics to relieve severe pain, sleep apneas, excessive sleepiness associated with a disease, obstructive sleep apnea, narcolepsy: sleepiness, excessive sleepiness, excessive sleepiness associated with narcolepsy; central nervous system disorders such as Parkinson's disease; for protecting cerebral tissue from ischemia; vigilance disorders including vigilance disorders associated with Steinert's disease, attention disorders, e.g. linked to hyperactivity (ADHD); tiredness and fatigue, particularly those associated with multiple sclerosis and other neurodegenerative diseases; depression, depressive mood linked to weak sunlight (sundowning); schizophrenia; shift work, time lag including jet lag; as well as food behaviour disorders, wherein modafinil acts as an appetite is stimulant.

All the references including patents and patents applications cited in the present application are incorporated herein by reference.

EXAMPLES

Preparation of Modafinil Solvates and Solvate Solid Solutions

Example 1

Preparation of Acetonitrile Solvate 40 g of modafinil form I were added to 2.5 L acetonitrile heated to reflux. The reaction mixture was stirred until dissolution was completed. The mixture was allowed to cool slowly to room temperature, typically by leaving it at room temperature, for about 24 hours without stirring. Monocrystals formed after a slow evaporation at room temperature, were isolated by filtration. The isolated solid was identified as the acetonitrile solvate by powder X-ray diffraction pattern. Yield: 90%.

Example 2

Preparation of Chloroform Solvate Solid Solution 20 g of modafinil were added to 2.5 L chloroform and heated to reflux. The reaction mixture was stirred for 0.5 hours until modafinil dissolution was completed. The mixture was allowed to cool slowly to room temperature for about 24 hours without stirring. Monocrystals formed after a slow evaporation at room temperature, were isolated by filtration. The isolated solid was identified as a monochloroform solvate solid solution by powder X-ray diffraction pattern. Yield: 90%.

Example 3

Preparation of Tetrahydrofuran (THF) Solvate Solid Solution 40 g of modafinil were added to 2.5 L THF and heated to reflux. The reaction mixture was stirred for 0.5 hours until modafinil dissolution was completed. The mixture was allowed to cool slowly to room temperature for about 24 hours without stirring. Monocrystals formed after a slow evaporation at room temperature, were isolated by filtration. The isolated solid was identified as a monotetrahydrofuran solvate solid solution by powder X-ray diffraction pattern. Yield: 90%.

Example 4

Preparation of Dioxane Solvate Solid Solution 20 g of modafinil were added to 2.5 L dioxane and heated to reflux. The reaction mixture was stirred for 0.5 hours until modafinil dissolution was completed. The mixture was allowed to cool slowly to room temperature for about 24 hours without stirring. Monocrystals formed after a slow evaporation at mom temperature, were isolated by filtration. The isolated solid was identified as a monodioxane solvate solid solution powder X-ray diffraction pattern. Yield: 92%.

Example 5

Preparation of Chloroform-THF Modafinil Solvate Solid Solution

Modafinil (3 g) was suspended in a mixture of 200 mL of THF and 200 mL of chloroform, in a three necked round bottom flask equipped with a reflux condenser, a thermometer, and an agitator. The reaction mixture is heated to reflux and stirred for 10 minutes until dissolution of modafinil was completed. The resulting solution was cooled to room temperature for about 24 hours without stirring. Modafinil chloroform-THF solvate solid solution was identified by powder X-ray diffraction pattern. Yield: 90%.

Example 6

Preparation of Chloroform-dioxane Modafinil Solvate Solid Solution

Modafinil (3 g) was suspended in a mixture of 200 mL of dioxane and 200 mL of chloroform, in a three necked round bottom flask equipped with a reflux condenser, a thermometer, and an agitator. The reaction mixture is heated to reflux and stirred for 10 minutes until dissolution of modafinil was completed. The resulting solution was cooled to room temperature for about 24 hours without stirring. Modafinil chloroform-dioxane solvate solid solution was identified by powder X-ray diffraction pattern. Yield: 90%.

Preparation of CRL 40476 form I (CRL 40476-[f I])

Examples 7-9

Preparation of Modafinil form I Via Crystallization Method

Example 7

10 g of modafinil were added to 77 mL of methanol heated to reflux. The reaction mixture was stirred for 0.5 hours at about 65° C. until modafinil dissolution was completed. The solution was allowed to cool slowly (−0.1° C./min) to −10° C. under stirring. The reaction mixture was filtered, and the isolated solid was then dried, affording modafinil form I with a 90% yield. Form I was identified by powder X-ray diffraction pattern.

Example 8

1 g of modafinil was added to 10 mL dimethylformamide and heated to reflux. The reaction mixture was stirred for 30 minutes until modafinil dissolution was completed. The reaction was allowed to cool slowly to room temperature for about 24 hours without stirring. Monocrystals formed by slow evaporation at room temperature, were isolated by filtration. The isolated solid was identified as form I by powder X-ray diffraction pattern. Yield:100%.

Example 9

1 g of modafinil was added to 50 mL of 2-methoxyethanol heated to reflux. The reaction mixture was stirred for 30 minutes at 120° C. until modafinil dissolution was completed. The solution was allowed to cool slowly (−0.1° C./min) to 10° C. under stirring. The reaction mixture was filtered, and the isolated solid was then dried, affording modafinil form I with a 93% yield. Form I was identified by powder X-ray diffraction pattern.

Examples 10-11

Preparation of Modafinil Form I Via Solvates Formation Method

Example 10

1 g of modafinil chloroform solvate prepared by the method of Example 2 may also be converted into CRL 40476 form I by suspending it in 20 ml of chloroform during 3 days. Powder X-ray diffraction pattern confirmed that the resulting material is crystalline modafinil as form I. Yield: 88%.

Example 11

1 g of modafinil THF solvate prepared by the method of Example 3 also may be converted into CRL 40476 form I by suspending it in 20 mL of acetone during 3 days Powder X-ray diffraction pattern confirmed that the resulting material is crystalline modafinil as form I. Yield: 87%.

Preparation of CRL 40476 form III (CRL 40476-[f III])

Examples 12-15

Preparation of Modafinil Form III Via Solvates Formation Method

Example 12

10 g of modafinil dioxane solvate solid solution prepared by the method of Example 4 were heated at 110° C. for 12 hours. The solid was identified as modafinil form III by X-ray diffractometry. The total yield of the reaction was 100%. Powder X-ray diffraction pattern confirmed the end product is crystalline CRL 40476 form III.

Example 13

10 g of modafinil chloroform solvate solid solution prepared by the method of Example 2 were heated at 130° C. for 12 hours. The solid was identified as modafinil form III by powder X-ray diffraction pattern. The yield of the reaction was 100%.

Example 14

10 g of modafinil THF solvate prepared by the method of Example 3 were heated at 130° C. for 12 hours. The solid was identified as modafinil form III by powder X-ray diffraction pattern. The yield of the reaction was 100%.

Example 15

10 g of modafinil acetonitrile solvate prepared by the method of Example 1 were heated at 130° C. for 12 hours. The solid was identified as modafinil form III by powder X-ray diffraction pattern. The total yield of the reaction was 100%.

Examples 16-19

Preparation of Modafinil Form III Via Crystallization Method

Example 16

97 g of modafinil were added to 759 mL of methanol heated to reflux until modafinil dissolution was completed. The reaction mixture was precipitated by adding 600 mL of water at 1° C. during 1 min. The reaction mixture was filtered, and the isolated solid was then dried, affording CRL 40476 form III as confirmed powder X-ray diffraction pattern, with a specific surface area of 0.34 $m^2$/mg (BET method). Yield: 92%.

Example 17

30 g of modafinil were added to 1.8 L of acetonitrile heated to reflux. The reaction mixture was stirred for 30 minutes at about 81° C. until modafinil dissolution was completed. The solution was allowed to cool (−10° C./min) to 5° C. under stirring. The reaction mixture was filtered, and isolated solid was then dried, affording CRL 40476 form III as confirmed by powder X-ray diffraction pattern, with a specific surface area of 0.99 $m^2$/g (BET method). Yield: 89.5%.

Example 18

30 g of modafinil were added to 1.8 L of tetrahydrofuran heated to reflux. The reaction mixture was stirred for 30 minutes at about 65° C. until modafinil dissolution was completed. The solution was allowed to cool (−10° C./min) to 5° C. under stirring. The reaction mixture was filtered, and isolated solid was then dried, affording CRL 40476 form III as confirmed by powder X-ray diffraction pattern with a yield of 84.5%.

Example 19

30 g of modafinil were added to 1.8 L of chloroform heated to reflux. The reaction mixture was stirred for 30 minutes at about 61° C. until modafinil dissolution was completed. The solution was allowed to cool (−10° C./min) to 5° C. under stirring. The reaction mixture was filtered, and isolated solid was then dried, affording modafinil form III as confirmed by powder X-ray diffraction pattern, with a yield of 82%.

Example 20

Preparation of Modafinil Form III Via Polymorphic Transition Method

Form V or form VI converts into modafinil form III upon gentle heating to about 110° C. followed by slow cooling. In both cases, form III was confirmed by powder X-ray diffraction pattern.

Preparation of CRL 40476 Form IV (CRL 40476-[f IV])

Examples 21-23

Preparation of Modafinil Form IV Via Solvates Formation Method

Example 21

10 g of THF solvate of modafinil prepared by the method of Example 3 were desolvated by air drying during 1 month. The solid was identified as modafinil form IV by powder X-ray diffraction pattern. The yield of the reaction was 95%.

Example 22

10 g of chloroform solvate of modafinil prepared by the method of Example 2 were desolvated by air drying during 1 month. The solid was identified as modafinil form IV by powder X-ray diffraction pattern. The total yield of the reaction was 94%.

Example 23

10 g of dioxane solvate of modafinil prepared by the method of Example 4 were desolvated by air drying during 1 month. The solid was identified as modafinil form IV by powder X-ray diffraction pattern. The yield of the reaction was 93%.

Example 24

Preparation of Modafinil Form IV Via Crystallization Method 25.1 g of modafinil were added to 900 mL methanol and heated to reflux until modafinil dissolution was completed. The reaction mixture was added to 2000 mL of water at 1° C. without stirring during 10 minutes. The reaction mixture was filtered, and the isolated solid was then dried, affording modafinil form IV according to its powder X-ray diffraction pattern with a 92% yield.

Preparation of CRL 40476 Form V (CRL 40476-[f V])

Examples 25-29

Preparation of Modafinil Form V Via Solvates Formation Method

Example 25

100 mg of modafinil THF solvate prepared by the method of Example 3 were heated at 60° C. for 5 hours. The solid was identified as CRL 40476 form V by powder X-ray diffraction pattern. The total yield of the reaction was 100%.

Example 26

100 g of modafinil chloroform solvate prepared by the method of Example 2 were heated either at 90° C. for 1 hour under vacuum (22 mmHg) or at 80° C. for 1 hour under vacuum (0.05 mmHg). In both experiments, the solid was identified as CRL 40476 form V by powder X-ray diffraction pattern. The total yield of the reaction was 100%.

Example 27

100 g of modafinil dioxane solvate prepared by the method of Example 2 were heated at 90° C. for 1 hour under vacuum (22 mmHg). The solid was identified as modafinil form V by powder X-ray diffraction patter. The total yield of the reaction was 100%.

Example 28

100 mg of modafinil THF-chloroform solvate solid solution prepared by the method of Example 5 were heated at 70° C. for 5 hours. The solid was identified as modafinil form V by powder X-ray diffraction pattern. The yield of the reaction was 100%.

Example 29

100 mg of modafinil dioxane-chloroform solvate solid solution prepared by the method of Example 6 were heated at 70° C. for 5 hours. The solid was identified as modafinil form V by powder X-ray diffraction pattern. The yield of the reaction was 100%.

Preparation of CRL 40476 Form VI (CRL 40476-[f VI])

Example 30

Preparation of Modafinil Form VI Via Solvates Formation Method

A 40 g sample of acetonitrile solvate of modafinil prepared by the method of Example 1 was dried under reduced pressure of 22 mmHg for 6 hours at about 20° C. The solid was identified as modafinil form VI by powder X-ray diffraction pattern. The total yield of the reaction was 100%.

Preparation of CRL 40476 Form VII (CRL 40476-[f VII])

Example 31

Crystallization of Modafinil Form VII Via Crystallization Method 0.5 g of modafinil was dissolved in 20 mL of acetone by heating up to the boiling point. In order to remove tiny insoluble particles, the clear solution was filtered on a glass filter n°3 and poured into an equal volume of cold water. After 12 hours of standing at room temperature (without stirring), fine platelets spontaneously appeared and were collected by filtration. The obtained phase, which was not a conglomerate nor a solvate, was identified as modafinil form VII by powder X-ray diffraction pattern.

Pharmacokinetic Studies

Material and Methods for Examples 32 and 33

A comparative bioavailability study was carried out in dogs to determine the pharmacokinetic profile of the new polymorphs form IV and form V of modafinil. The study was aimed to compare plasma levels of polymorphs form IV and form V versus the reference form I. Six male beagle dogs were randomly assigned to three groups according to a (3×3) Latin-square design. Each group was administered a single oral 30 mg/kg body weight dose of either form IV or form V or the reference form I and two successive administrations were separated by a one-week wash-out period according to the protocol design reported table I.

TABLE I

| | Administration protocol | | |
|---|---|---|---|
| | Period 1 Day 1 | Period 2 Day 8 | Period 3 Day 15 |
| Dog 1 | B | C | A |
| Dog 2 | C | A | B |
| Dog 3 | A | B | C |
| Dog 4 | C | B | A |
| Dog 5 | B | A | C |
| Dog 6 | A | C | B |

Where
A = form I,
B = form IV,
C = form V

Dogs were fasted overnight prior dosing and food was returned to them four hours after dosing. Blood samples were collected after each dose by venepuncture at predose (within one hour of dosing) and at 0.5, 1, 1.5, 2, 2.5, 3, 4, 5.5, 7, 9 and 24 hours post-dose. Blood samples were collected on hepadnized test tubes and immediately centrifuged at 3,000 rpm. Then plasma was drawn off and stored frozen (−20° C.) until analyzed. Plasma concentrations of modafinil were determined by validated high-pressure liquid chromatography according to the method of Moachon G. et al. (J. Chromatog. B 1994; 654:91). Pharmacokinetic parameters were determined using noncompartimental analysis.

Example 32

Results: Bioavailability Profile of CRL 40476 form IV

Results from the form IV versus form I comparison indicated that systemic exposure ($C_{max}$ and $AUC_{0-24h}$) was substantially higher after administration of modafinil polymorph form IV than after that of modafinil form I, when both given to the dogs at equivalent dose (i.e.: dose=30 mg/kg given by oral route). With respect to form IV, the plasma levels of unchanged modafinil (that means quantity of drug available at the sites of action) are higher than plasma levels of reference form I, as reported table 2:

TABLE 2

| Form | $C_{max}$ (µg/ml) | $C_{4h}$ (µg/ml) | $AUC_{0-24h}$ (h · µg/ml) | Normalized AUC |
|---|---|---|---|---|
| I | 18.60 ± 2.30 | 15.37 ± 2.56 | 164.80 ± 23.75 | 5.49 |
| IV | 24.98 ± 1.12 | 21.23 ± 1.88 | 200.69 ± 18.09 | 6.69 |

Data are expressed as mean ± standard error of mean (SEM) for each treatment group, $C_{max}$ = maximum plasma level of modafinil, $C_{4h}$ = plasma level measured at 4 hours post-dose, $AUC_{0-24h}$ = area under the curve C = f(t) calculated by the trapezoidal rule from 0 to 24 hours post-dose, Normalized AUC = $AUC_{0-24h}$ per 1 mg/kg.

When compared to the reference form (CRL 40476 form I), the new crystalline form IV appears to have a better resorption rate and a higher bioavailability. It is well known that, for many medications including modafinil, comparative bioavailability studies carried out in dogs, are highly relevant models to translate the pharmacokinetic profile (namely differences in AUC) into humans with proportional (to body weight or body surface area) replication into patients.

As a consequence, modafinil form IV may advantageously replace modafinil form I to increase the extent of oral absorption of modafinil without delaying or modifying the onset of therapeutic action of modafinil (on hypersomnolence states as in narcoleptic patients for example or in any other therapeutic indication).

The crystalline form IV of modafinil described herein may be formulated into appropriate pharmaceutical compositions in replacement of form I. Using such pharmaceutical compositions (oral route), an equivalent therapeutic effect may be achieved at lower dosages, thereby increasing the benefit/risk ratio of modafinil by reducing for example the modafinilCytochrome p450 interactions, such interactions being sources of potential deleterious or cumbersome drug-drug interactions.

Example 33

Bioavailability Profile of CRL 40476 Form V

Example 32 results originated from the same study design as for form IV (refer to example 31 above).

When compared to the reference form (CRL 40476 form I), the new crystalline form V is characterized by a faster absorption/resorption rate. At equivalent administered dose (i.e.: dose=30 mg/kg given by oral route in dog), higher plasma levels of unchanged modafinil (that means quantity of drug available at the sites of action) are achieved earlier than plasma levels induced by reference form I as shown in table 3:

TABLE 3

| Form | MRT (h) | $C_{1h}$ (µg/ml) | $C_{1.5h}$ (µg/ml) | $C_{2h}$ (µg/ml) | $C_{2.5h}$ (µg/ml) | $C_{max}$ (µg/ml) | $T_{max}$ (h) |
|---|---|---|---|---|---|---|---|
| I | 6.91 ± 0.53 | 8.81 ± 2.45 | 12.73 ± 2.39 | 14.16 ± 2.23 | 14.23 ± 1.95 | 18.60 ± 2.30 | 3.00 |
| V | 6.11 ± 0.36 | 12.41 ± 2.07 | 15.31 ± 2.06 | 16.56 ± 2.48 | 16.37 ± 2.38 | 18.72 ± 2.09 | 1.67 |

Data are expressed as mean ± standard error of mean (SEM), Tmax values are given as mean, $C_{xh}$ = plasma level measured at x hours post-dose, MRT = mean residence time, Tmax = time to reach peak plasma level of modafinil.

After administration of an equivalent oral dose of modafinil, the Tmax value obtained in this study for form V was substantially shorter (in fact a~50% reduction in time needed to reach the concentration Cmax) than that obtained with the reference form I. In addition, over the 0 to 2.5 hour period post-dose, the mean individual concentration values for form V are substantially greater than the corresponding mean concentration values for form I indicating that the oral resorption appeared to be more rapid following administration of form V. The maximum plasma concentration is likely achieved earlier following the administration of form V than following the administration of an equivalent dose of form I. It is well known that, for many medications including modafinil, comparative bioavailability studies carried out in dogs, are a highly relevant model to translate the pharmacokinetic profile (namely differences in Tmax) into humans with proportional (to body weight or body surface area) replication into patients.

As a consequence, by replacing modafinil racemate form I by modafinil racemate form V, the delay of therapeutic action of modafinil (on hypersomnolence states as in narcoleptic patients for example or in any other therapeutic indication) is reduced. According to the data shown in Table 3, form V is characterized by a mean Tmax value equal to about 50% of the one known for reference polymorph I. As such, the onset of therapeutic effect achieved with treatment comprising form V is also decreased by 50%, becoming namely 2.2 hours to 2.5 hours (instead of 4.0-5.0 hours with form I).

The crystalline form V of modafinil described herein may be formulated into appropriate pharmaceutical compositions in replacement of form I. The use of such form of modafinil with reduced delay of action is of interest in all pathological situations where it is important to restore rapidly a normal vigilance level (narcoleptic patients particularly when hypersomnolence episode appears during social or professional life, fatigue syndrome, shift work, jet lag, etc.).

What is claimed:

1. A method for preparing modafinil solvates comprising: i) dissolving any physical species of modafinil in a solvent selected from the group consisting of acetonitrile, tetrahydrofaran, chloroform and dioxane, or mixtures thereof; and ii) crystallizing modafinil solvate from the solvent.

2. A method for preparing CRL 40476 form I with high purity via direct crystallization consisting essentially of: i) dissolving modafinil in a solvent selected from the group consisting of 2-methoxyethanol, ethanol, acetone, N,N-dimethylformamide or in a mixture of water with one of these solvents; ii) crystallizing by evaporating a portion of this solution, or crystallizing by regular controlled cooling of the previous solution below 20° C.; and iii) separating modafinil CRL 40476 form I from the solvent.

3. A method for preparing CRL 40476 form III comprising: i) preparing a modafinil solvate from a solvent selected from the group consisting of dioxane, chloroform, tetrahydrofuran, or a mixture thereof, and acetonitrile; and ii) desolvating the modafinil solvate to obtain CRL 40476 form III by heating the resulting modafinil solvate at a temperature in the range of 1 IOC° to 140C' under atmospheric pressure.

4. A method for preparing CRL 40476 form III with high purity via direct crystallization comprising: i) dissolving modafinil in a solvent selected from the group consisting of acetonitrile, chloroform, tetrahydrofuran and methanol; ii) crystallizing modafinil from the solvent, in the case of acetonitrile, chloroform, or tetrahydrofuran, by cooling rapidly, in the case of methanol, either by cooling rapidly, or by precipitating modafinil by adding one to nine volumes of water to the methanol solution under stirring; and iii) separating the solvent to obtain CRL 40476 form III.

5. A method for preparing CRL 40476 form III with high purity comprising: i) heating CRL 40476 form V,CRL 40476 form VI or any modafinil solvate to a temperature from 110° C. to 130° C.; and ii) cooling at room temperature for a sufficient time to complete the conversion.

6. A method for preparing CRL 40476 form IV comprising: i) preparing a modafinil solvate from a solvent selected from the group consisting of tetrahydrofuran, chloroform, dioxane and a mixture thereof; and ii) desolvating the modafinil solvate to obtain CRL 40476 form IV.

7. A method for preparing CRL 40476 form IV with high purity via direct crystallization comprising: i) dissolving modafinil in methanol; ii) crystallizing modafinil from the solvent, by adding a volume of water in the range of 50/150 to 90/10 (v/v) to the methanol solution without stirring; and iii) separating the solvent to obtain CRL 40476 form IV.

8. A method for preparing CRL 40476 form V comprising: i) preparing a modafinil solvate from a solvent selected from the group consisting of tetrahydrofuran, dioxane and chloroform, or a mixture thereof, and ii) desolvating the modafinil solvate to obtain CRL 40476 form V.

9. A method according to claim 8, wherein the selected solvent is tetrahydrofuran, and the desolvation is performed by filtering and heating the modafinil solvate to a temperature in the range of 40° C. to 70° C.

10. A method according to claim 8, wherein the selected solvent is dioxane, and the desolvation is performed by filtering and heating the modafinil solvate to a temperature in the range of 60° C. to 90° C.

11. A method according to claim 8, wherein the selected solvent is chloroform, and the desolvation is performed by filtering and heating the modafinil solvate to a temperature in the range of 70° C. to 100° C.

12. A method for preparing CRL 40476 form VI comprising: i) preparing a modafinil solvate from acetonitrile; and ii) desolvating the modafinil solvate to obtain CRL 40476 form VI, at a temperature from 10° C. to 30° C., under atmospheric pressure.

13. An acetonitrile solvate of modafinil that produces a powder X-ray diffraction pattern with interplanar d-spacing at 13.3, 9.93, 8.62, 7.98, 7.50, 6.87, 6.58, 6.33, 5.87, 5.65, 5.45, 5.22, 5.12, 4.87, 4.62, 4.50, 4.42, 4.37, 4.30, 4.21, 4.15, 4.05, 3.95, 3.87, 3.64, 3.59, 3.54, 3.445, 3.368, 3.278, 3.243, 3.153, 3.068 (Å).

14. A modafinil solvate solid solution having a formula of:

Modafinil-[Tetrahydrofuran$_x$, -Chloroform$_y$-Dioxane$_z$] where x, y and z are defined by:

$$\begin{bmatrix} 0 \leq x \leq 1 \\ 0 \leq y \leq 1 \\ 0 \leq z \leq 1 \\ x+y+z=1 \end{bmatrix}.$$

15. A tetrahydrofuran modafinil solvate solid solution of claim 14 where x=1 that produces a powder X-ray diffraction pattern with interplanar d-spacing at 13.2, 9.93, 8.66, 8.19, 6.59, 6.33, 5.88, 5.44, 5.21, 5.10, 4.85, 4.49, 4.42, 4.31, 4.15, 4.04, 3.95, 3.87, 3.64, 3.59, 3.388, 3.358, 3.285, 3.248, 3.140, 3.067, 3.022 (Å).

16. A chloroform modafinil solvate solid solution of claim 14 where y=1 that produces a powder X-ray diffraction pattern with inter-planar d-spacing at 12.5, 7.91, 6.27, 5.61, 4.92, 4.44, 4.29, 4.18, 3.96, 3.54, 3.484, 3.294, 3.136, 3.041 (Å).

17. A dioxane modafinil solvate solid solution of claim 16 where z=1 that produces a powder X-ray diffraction pattern with interplanar d-spacing at 12.7, 9.02, 8.03, 6.37, 5.69, 5.00, 4.50, 4.36, 4.24, 4.02, 3.61, 3.54, 3.181, 3.002 (Å).

18. A chloroform-tetrahydrofuran modafinil solvate solid solution of claim 14 where x+y=1 and prepared from a 1/1 (v/v) chloroform-tetrahydrofuran solution, that produces a powder X-ray diffraction pattern with interplanar d-spacing at 12.6, 7.98, 6.29, 5.86, 5.65, 5.45, 5.01, 4.95, 4.68, 4.47, 4.35, 4.21, 4.09, 3.99, 3.64, 3.57, 3.51, 3.361, 3.277, 3.150 (Å).

19. A chloroform-dioxane modafinil solvate solid solution of claim 14 where y+z=1 and prepared from a 1/1 (v/v) chloroform-dioxane solution, that produces a powder X-ray diffraction pattern with interplanar d-spacing at 12.5, 9.82, 8.67, 7.97, 7.45, 6.78, 6.26, 5.84, 5.63, 5.43, 5.09, 4.94, 4.65, 4.46, 4.36, 4.19, 4.08, 3.97, 3.76, 3.64, 3.55, 3.497, 3.418, 3.353, 3.269, 3.220, 3.141 (Å).

* * * * *